US009579140B2

(12) United States Patent
Jones et al.

(10) Patent No.: US 9,579,140 B2
(45) Date of Patent: *Feb. 28, 2017

(54) INSTRUMENTS AND METHODS FOR ADJUSTING SEPARATION DISTANCE OF VERTEBRAL BODIES WITH A MINIMALLY INVASIVE SPINAL STABILIZATION PROCEDURE

(71) Applicant: Zimmer Spine, Inc., Minneapolis, MN (US)

(72) Inventors: Robert J. Jones, Cedar Park, TX (US); Charles R. Forton, Frisco, TX (US)

(73) Assignee: Zimmer Spine, Inc., Edina, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/748,005

(22) Filed: Jun. 23, 2015

(65) Prior Publication Data

US 2015/0297277 A1 Oct. 22, 2015

Related U.S. Application Data

(63) Continuation of application No. 14/164,359, filed on Jan. 27, 2014, now Pat. No. 9,066,762, which is a (Continued)

(51) Int. Cl.
*A61B 17/88* (2006.01)
*A61B 17/02* (2006.01)
(Continued)

(52) U.S. Cl.
CPC ........ *A61B 17/8866* (2013.01); *A61B 17/025* (2013.01); *A61B 17/7002* (2013.01);
(Continued)

(58) Field of Classification Search
CPC ............ A61B 17/7032; A61B 17/7037; A61B 17/7062; A61B 17/7082; A61B 17/88
(Continued)

(56) References Cited

U.S. PATENT DOCUMENTS 4,898,161 A 2/1990 Grundei
6,090,113 A 7/2000 Le Couedic et al.
(Continued)

FOREIGN PATENT DOCUMENTS

DE 10125717 A1 12/2002
EP 0528177 A2 2/1993
(Continued)

OTHER PUBLICATIONS

"U.S. Appl. No. 11/002,931, Examiner Interview Summary mailed Mar. 25, 2008", 4 pgs.
(Continued)

*Primary Examiner* — Mary Hoffman
*Assistant Examiner* — Tara R Carter
(74) *Attorney, Agent, or Firm* — Schwegman Lundberg & Woessner, P.A.

(57) ABSTRACT

A spinal stabilization system may be formed in a patient. In some embodiments, a minimally invasive procedure may be used to form a spinal stabilization system in a patient. Bone fastener assemblies may be coupled to vertebrae. Each bone fastener assembly may include a bone fastener and a collar. Extenders may be coupled to the collar to allow for formation of the spinal stabilization system through a small skin incision. The extenders may allow for alignment of the collars to facilitate insertion of an elongated member in the collars. An elongated member may be positioned in the collars and a closure member may be used to secure the elongated member to the collars. An adjuster may be used in conjunction with the extenders to change a separation distance between the bone fastener assemblies.

20 Claims, 25 Drawing Sheets

Related U.S. Application Data continuation of application No. 13/486,232, filed on Jun. 1, 2012, now Pat. No. 8,636,743, which is a continuation of application No. 12/623,204, filed on Nov. 20, 2009, now Pat. No. 8,192,440, which is a continuation of application No. 11/002,931, filed on Dec. 2, 2004, now Pat. No. 7,811,288.

(51) Int. Cl.
  *A61B 17/16* (2006.01)
  *A61B 17/17* (2006.01)
  *A61B 17/70* (2006.01)
  *A61B 17/86* (2006.01)

(52) U.S. Cl.
  CPC ...... *A61B 17/7032* (2013.01); *A61B 17/7079* (2013.01); *A61B 17/7083* (2013.01); *A61B 17/7085* (2013.01); *A61B 17/7091* (2013.01); *A61B 17/861* (2013.01); *A61B 17/16* (2013.01); *A61B 17/1655* (2013.01); *A61B 17/1757* (2013.01); *A61B 17/7011* (2013.01); *A61B 17/7037* (2013.01); *A61B 17/8605* (2013.01); *A61B 17/8875* (2013.01); *A61B 2017/0256* (2013.01); *A61B 2090/037* (2016.02)

(58) Field of Classification Search
  USPC ...... 606/86 A, 86 R, 99, 104, 105, 250–279; 600/206, 207, 210, 213, 217, 227
  See application file for complete search history.

(56) References Cited

U.S. PATENT DOCUMENTS

| | | | |
|---|---|---|---|
| 6,530,929 | B1 | 3/2003 | Justis et al. |
| 6,669,699 | B2 | 12/2003 | Ralph et al. |
| 6,716,218 | B2 | 4/2004 | Holmes et al. |
| 6,740,087 | B2 | 5/2004 | Knox |
| 6,926,718 | B1 | 8/2005 | Michelson |
| 7,004,947 | B2 | 2/2006 | Shluzas et al. |
| 7,008,432 | B2 | 3/2006 | Schläpfer et al. |
| 7,160,300 | B2 | 1/2007 | Jackson |
| 7,188,626 | B2 | 3/2007 | Foley et al. |
| 7,250,052 | B2 | 7/2007 | Landry et al. |
| 7,465,306 | B2 | 12/2008 | Pond, Jr. et al. |
| 7,491,218 | B2 | 2/2009 | Landry et al. |
| 7,578,822 | B2 | 8/2009 | Rezach et al. |
| 7,618,424 | B2 | 11/2009 | Wilcox et al. |
| 7,618,442 | B2 | 11/2009 | Spitler et al. |
| 7,621,918 | B2 | 11/2009 | Jackson |
| 7,691,132 | B2 | 4/2010 | Landry et al. |
| 7,758,617 | B2 | 7/2010 | Iott et al. |
| 7,811,288 | B2 * | 10/2010 | Jones ................ A61B 17/7091 606/279 |
| 7,914,536 | B2 | 3/2011 | Macdonald et al. |
| 8,034,084 | B2 | 10/2011 | Landry et al. |
| 8,172,855 | B2 | 5/2012 | Abdou |
| 8,192,440 | B2 * | 6/2012 | Jones ................ A61B 17/7091 606/86 A |
| 8,636,743 | B2 * | 1/2014 | Jones ................ A61B 17/7091 606/279 |
| 8,668,699 | B2 | 3/2014 | Thomas et al. |
| 9,066,762 | B2 * | 6/2015 | Jones ................ A61B 17/7091 |
| 2002/0160368 | A1 | 10/2002 | Bass et al. |
| 2002/0161368 | A1 | 10/2002 | Foley et al. |
| 2003/0187453 | A1 | 10/2003 | Schlapfer et al. |
| 2004/0138662 | A1 | 7/2004 | Landry et al. |
| 2004/0143265 | A1 | 7/2004 | Landry et al. |
| 2004/0172022 | A1 | 9/2004 | Landry et al. |
| 2006/0036244 | A1 | 2/2006 | Spitler et al. |
| 2006/0036255 | A1 | 2/2006 | Pond, Jr. et al. |
| 2006/0084993 | A1 | 4/2006 | Landry et al. |
| 2006/0095035 | A1 | 5/2006 | Jones et al. |
| 2006/0111713 | A1 | 5/2006 | Jackson |
| 2006/0142761 | A1 | 6/2006 | Landry et al. |
| 2006/0149278 | A1 | 7/2006 | Abdou |
| 2006/0217735 | A1 | 9/2006 | Macdonald et al. |
| 2006/0235427 | A1 | 10/2006 | Thomas et al. |
| 2006/0247630 | A1 | 11/2006 | Iott et al. |
| 2006/0247645 | A1 | 11/2006 | Wilcox et al. |
| 2006/0247649 | A1 | 11/2006 | Rezach et al. |
| 2007/0239159 | A1 | 10/2007 | Altarac et al. |
| 2008/0077155 | A1 | 3/2008 | Diederich |

FOREIGN PATENT DOCUMENTS

| | | |
|---|---|---|
| WO | WO-2005107415 A2 | 11/2005 |
| WO | WO-2005107415 A3 | 1/2006 |
| WO | WO-2006060430 A1 | 6/2006 |
| WO | WO-2006091863 A2 | 8/2006 |
| WO | WO-2006091863 A3 | 8/2006 |

OTHER PUBLICATIONS

"U.S. Appl. No. 11/002,931, Final Office Action mailed Jul. 15, 2008", 15 pgs.
"U.S. Appl. No. 11/002,931, Final Office Action mailed Jul. 21, 2009", 9 pgs.
"U.S. Appl. No. 11/002,931, Non Final Office Action mailed Jan. 10, 2008", 9 pgs.
"U.S. Appl. No. 11/002,931, Non Final Office Action mailed Jan. 13, 2010", 5 pgs.
"U.S. Appl. No. 11/002,931, Non Final Office Action mailed Dec. 16, 2008", 13 pgs.
"U.S. Appl. No. 11/002,931, Notice of Allowance mailed Jun. 30, 2010", 4 pgs.
"U.S. Appl. No. 11/002,931, Response filed Mar. 3, 2010 to Non Final Office Action mailed Jan. 3, 2010", 7 pgs.
"U.S. Appl. No. 11/002,931, Response filed Mar. 11, 2009 to Non Final Office Action mailed Dec. 16, 2008", 12 pgs.
"U.S. Appl. No. 11/002,931, Response filed Apr. 10, 2008 to Non Final Office Action mailed Jan. 10, 2008", 10 pgs.
"U.S. Appl. No. 11/002,931, Response filed Sep. 22, 2009 to Final Office Action mailed Jul. 21, 2009", 9 pgs.
"U.S. Appl. No. 11/002,931, Response filed Oct. 15, 2008 to Final Office Action mailed Jul. 15, 2008", 17 pgs.
"U.S. Appl. No. 12/183,967, Non Final Office Action mailed May 25, 2011", 11 pgs.
"U.S. Appl. No. 12/623,204, Non Final Office Action mailed Oct. 4, 2011", 11 pgs.
"U.S. Appl. No. 12/623,204, Notice of Allowance mailed Feb. 13, 2012", 5 pgs.
"U.S. Appl. No. 12/623,204, Preliminary Amendment filed Jan. 21, 2010", 6 pgs.
"U.S. Appl. No. 12/623,204, Response filed Jan. 4, 2012 to Non Final Office Action mailed Oct. 4, 2011", 7 pgs.
"U.S. Appl. No. 13/486,232, Non Final Office Action mailed Mar. 22, 2013", 6 pgs.
"U.S. Appl. No. 13/486,232, Notice of Allowance mailed Sep. 18, 2013", 6 pgs.
"U.S. Appl. No. 13/486,232, Response filed Jun. 19, 2013 to Non Final Office Action mailed Mar. 22, 2013", 9 pgs.
"U.S. Appl. No. 14/164,359, Non Final Office Action mailed Apr. 10, 2014", 8 pgs.
"U.S. Appl. No. 14/164,359, Notice of Allowance mailed Feb. 24, 2015", 5 pgs.
"U.S. Appl. No. 14/164,359, Notice of Non Compliant Amendment mailed Aug. 27, 2014", 2 pgs.
"U.S. Appl. No. 14/164,359, Response filed Jun. 11, 2014 to Non Final Office Action mailed Apr. 10, 2014", 4 pgs.
"U.S. Appl. No. 14/164,359, Response filed Oct. 27, 2014 to Notice of Non Compliant Amendment mailed Aug. 27, 2014", 5 pgs.
"European Application Serial No. 10005583.9, Extended European Search Report mailed Sep. 29, 2010", 6 pgs.

(56) References Cited

OTHER PUBLICATIONS

"International Application Serial No. PCT/US2005/043199, International Preliminary Report on Patentability mailed Jun. 5, 2007", 7 pgs.

"International Application Serial No. PCT/US2005/043199, International Search Report mailed Apr. 6, 2006", 3 pgs.

"International Application Serial No. PCT/US2005/043199, Written Opinion mailed Apr. 6, 2006", 6 pgs.

"International Application Serial No. PCT/US2009/046567, International Preliminary Report on Patentability mailed Feb. 10, 2011", 10 pgs.

"International Application Serial No. PCT/US2009/046567, International Search Report mailed Oct. 2, 2009", 5 pgs.

"International Application Serial No. PCT/US2009/046567, Written Opinion mailed Oct. 2, 2009", 8 pgs.

"System Designed to Simplify the Correction of Spinal Deformities . . . ", Medical News Today, [Online]. Retrieved from the Internet: <www.medicalnewstoday.com>, (Jun. 2, 2008), 2 pgs.

Beringer, Will Forest, et al., "Anterior Transvertebral Interbody Cage with Posterior Transdiscal Pedicle Screw Instrumentation for High-Grade Spondylolisthesis", Neurosug Focus, vol. 20, (Mar. 2006), 3 pgs.

Kozak, Jeffrey A, et al., "Discussion: Isthmic Spondylolisthesis: Reduction vs. In-Situ Fusion?", SpineUniverse, [Online]. Retrieved from the Internet: <URL:http//www.spineuniverse.com>, (Jun. 2, 2008), 3 pgs.

La Rosa, Giovanni, et al., "Posterior Fusion and Implantation of the SOCON-SRI System in the Treatment of Adult Spondylolisthesis", Neurosurg Focus, Vo. 7, (1999), 11 pgs.

Palmer, Sylvain, et al., "Bilateral Decompressive Surgery in Lumbar Spinal Stenosis Associated with Spondylolisthesis: Unilateral Approach and Use of a Microscope and Tubular Retractor System", Neurosurg Focus, vol. 13, (Jul. 2002), 1-6.

Rengachary, Setti S, et al., "Reduction of Spondylolisthesis", Neurosurg Focus, vol. 13, (Jul. 2002), 1-3.

* cited by examiner

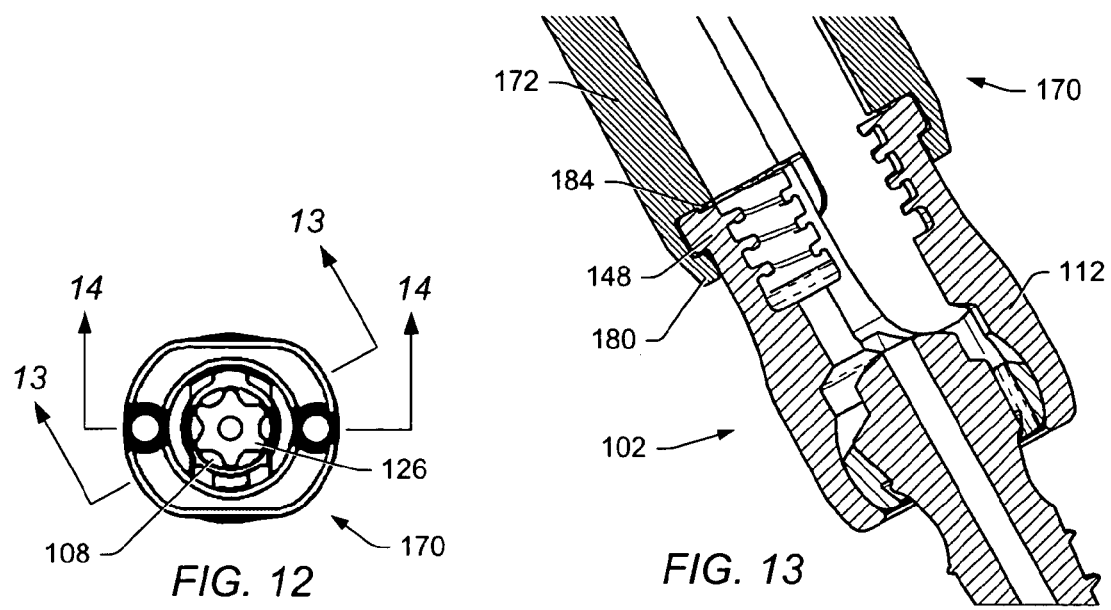
FIG. 12
FIG. 13
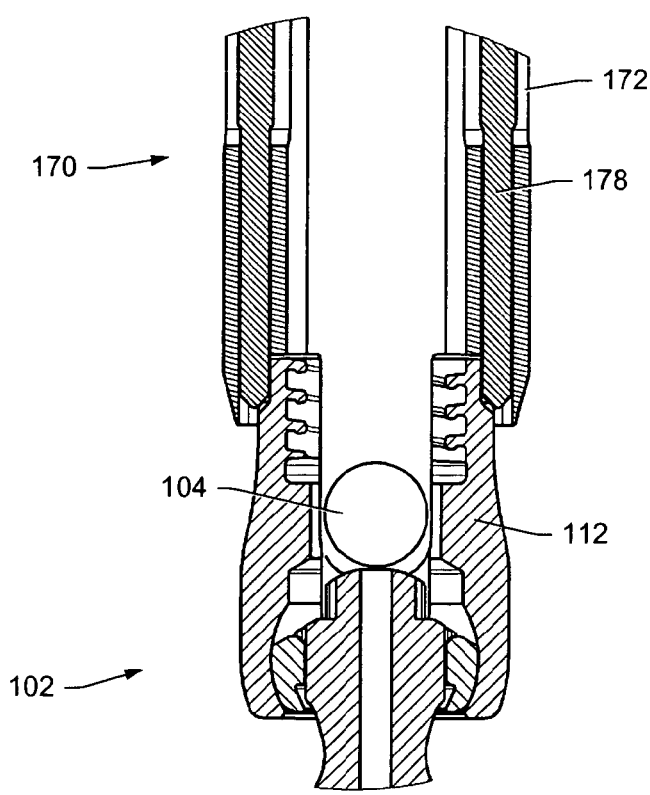
FIG. 14

INSTRUMENTS AND METHODS FOR ADJUSTING SEPARATION DISTANCE OF VERTEBRAL BODIES WITH A MINIMALLY INVASIVE SPINAL STABILIZATION PROCEDURE

CROSS-REFERENCE TO RELATED APPLICATION

This application is a continuation of U.S. patent application Ser. No. 14/164,359, filed Jan. 27, 2014, which is a continuation of Ser. No. 13/486,232, filed Jun. 1, 2012, now U.S. Pat. No. 8,636,743, issued Jan. 28, 2014, which is a continuation of U.S. patent application Ser. No. 12/623,204, filed Nov. 20, 2009, now U.S. Pat. No. 8,192,440, issued Jun. 5, 2012, which is a continuation of U.S. patent application Ser. No. 11/002,931, filed Dec. 2, 2004, now U.S. Pat. No. 7,811,288, issued Oct. 12, 2010, the contents of which are fully incorporated herein by reference.

BACKGROUND

Field of the Invention

The present invention generally relates to instruments and methods used during a spinal stabilization procedure to manipulate vertebrae. More particularly, the present invention generally relates to spinal surgical procedures that use instruments and methods for adjusting a separation distance between adjacent vertebrae.

Description of Related Art

Bone may be subject to degeneration caused by trauma, disease, and/or aging. Degeneration may destabilize bone and affect surrounding structures. For example, destabilization of a spine may result in alteration of a desired spacing between adjacent vertebrae. Alteration of a desired spacing between adjacent vertebrae may subject nerves that pass between vertebral bodies to pressure. Pressure applied to the nerves may cause pain and/or nerve damage. Maintaining the desired spacing between vertebrae may reduce pressure applied to nerves that pass between vertebral bodies. A spinal stabilization procedure may be used to establish and/or maintain the desired spacing between vertebrae and promote spinal stability.

Spinal stabilization may involve accessing a portion of the spine through soft tissue. Conventional stabilization systems may require a large incision and/or multiple incisions in the soft tissue to provide access to a portion of the spine to be stabilized. Conventional procedures may result in trauma to the soft tissue, for example, due to muscle stripping.

U.S. Pat. No. 6,530,929 to Justis et al. (hereinafter "Justis"), which is incorporated by reference as if fully disclosed herein, describes minimally invasive techniques and instruments for stabilizing a bony structure in an animal subject. Justis provides a method for using an instrument to connect at least two bone anchors with a connecting element. The instrument is secured to the anchors and manipulated to place the connecting element in a position more proximate the anchors. The Justis system is a constrained system. An elongated member installed using the Justis instruments and method must have a set curvature to function with the installation instruments.

U.S. Patent Publication No. U.S. 20040138662 to Landry et al. (hereinafter "Landry"), which is incorporated by reference as if fully disclosed herein, describes a minimally invasive procedure and instruments for stabilizing a portion of the spine. The Landry system is not a constrained system. An elongated member installed using the Landry instruments and method does not need to have a curvature defined by the insertion instruments.

SUMMARY

A spinal stabilization system may be installed in a patient to stabilize a portion of a spine. A spinal stabilization system may be installed using a minimally invasive procedure. An instrumentation kit may provide instruments and spinal stabilization system components necessary for forming a spinal stabilization system in a patient. The instrumentation kit may include one or more adjusters. An adjuster may change a separation distance between adjacent vertebrae. In some embodiments, the adjuster may be a compressor used to reduce a separation distance between vertebrae. In some embodiments, the adjuster may be a distractor used to increase a separation distance between vertebrae.

A spinal stabilization system may be used to achieve rigid pedicle fixation while minimizing the amount of damage to surrounding tissue. In some embodiments, a spinal stabilization system may be used to provide stability to two or more vertebrae. A spinal stabilization system may include an elongated member, two or more bone fastener assemblies, and/or a closure member.

A bone fastener assembly may include, but is not limited to, a bone fastener and a collar. A first portion of the bone fastener may couple to a vertebra. A first portion of a collar may couple to a second portion of the bone fastener. A second portion of the collar may couple to an elongated member during use. In some embodiments, the bone fastener may be able to rotate relative to the collar prior to insertion of the elongated member. After the bone fastener is placed in a vertebral body, the collar coupled to the bone fastener may be positioned so that the elongated member can be placed in the collar and in at least one other collar that is coupled to another vertebral body by a bone fastener.

During some spinal stabilization procedures, a spinal implant or other device may be inserted using an anterior approach, lateral approach or posterior approach. To stabilize the spinal implant or other device, a stabilization system may be installed using a posterior approach. In some embodiments, the spinal stabilization system may be installed using a minimally invasive surgical procedure where the stabilization system is installed through a small incision formed in the patient. During some surgical procedures, movement of vertebrae closer together may be desired to secure the position of an installed spinal implant or other device and/or to promote bone growth. During some surgical procedures, movement of vertebrae farther apart may be desired to provide a desired spacing between the vertebrae and/or to allow working room for manipulation of a device positioned between the vertebrae. An adjuster may be used with instruments used to install the spinal stabilization system to change the position of vertebrae coupled together by the spinal stabilization system. The adjuster may allow a closure member to be secured to a collar of the spinal stabilization system while a desired separation distance is maintained between the vertebrae.

A system for adjusting a distance between vertebral bodies may include a first extender coupled to a first bone fastener assembly. The first bone fastener assembly may be secured to a first vertebral body. A closure member may secure an elongated member to the first bone fastener assembly to inhibit movement of the elongated member relative to the first bone fastener assembly. The system may include a second extender coupled to a second bone fastener assembly that is secured to a second vertebral body. The system may include an adjuster. A portion of the adjuster may couple to the first extender. The system may include a driver. The driver may be coupled to the adjuster and to the second extender. A closure member coupled to the driver may be loosely threaded on the second bone fastener assembly such that the bone fastener assembly is able to move along the elongated member. The adjuster may rotate the driver to allow the driver to move the second extender relative to the elongated member to adjust the separation distance between the first vertebral body and the second vertebral body. In some embodiments, an axis of rotation of the adjuster may be offset from the driver to allow the adjuster to accommodate elongated members with various curvatures. When the desired separation distance is established, the driver may be used to secure the closure member to the elongated member and second bone fastener assembly.

In some embodiments, the adjuster may include an engagement mechanism. In a first position, the engagement mechanism may allow a first handle of the adjuster to translate towards or away from a second handle of the adjuster. In a second position, the engagement mechanism may inhibit translation of the first handle relative to the second handle. The engagement mechanism may facilitate coupling the adjuster and the driver to the first extender and the second extender. In embodiments where the adjuster is a compressor, the engagement mechanism may also allow a user to establish a separation distance between the driver and an end surface of the compressor. The established separation distance may allow the driver to rotate towards the compressor to allow for compression of the vertebral bodies.

Imaging techniques may be used to confirm the position of the installed spinal stabilization system. When the spinal stabilization system is positioned as desired, a driver may be used to shear off tool portions of closure members. A counter torque wrench may be used to counteract force applied to the spinal stabilization system so that the force applied to shear the tool portion of a closure member is not transmitted to the patient.

BRIEF DESCRIPTION OF THE DRAWINGS

Advantages of the present invention will become apparent to those skilled in the art with the benefit of the following detailed description and upon reference to the accompanying drawings in which:

FIG. 12 depicts a top view of an embodiment of a multi-channel extender with a bone fastener assembly coupled to the extender.

FIG. 13 depicts a cross-sectional representation of a portion of the extender and bone fastener assembly taken substantially along line 13-13 of FIG. 12.

FIG. 14 depicts a cross-sectional representation of a portion of the extender with the bone fastener assembly taken substantially along line 14-14 of FIG. 12.

Figure 1:
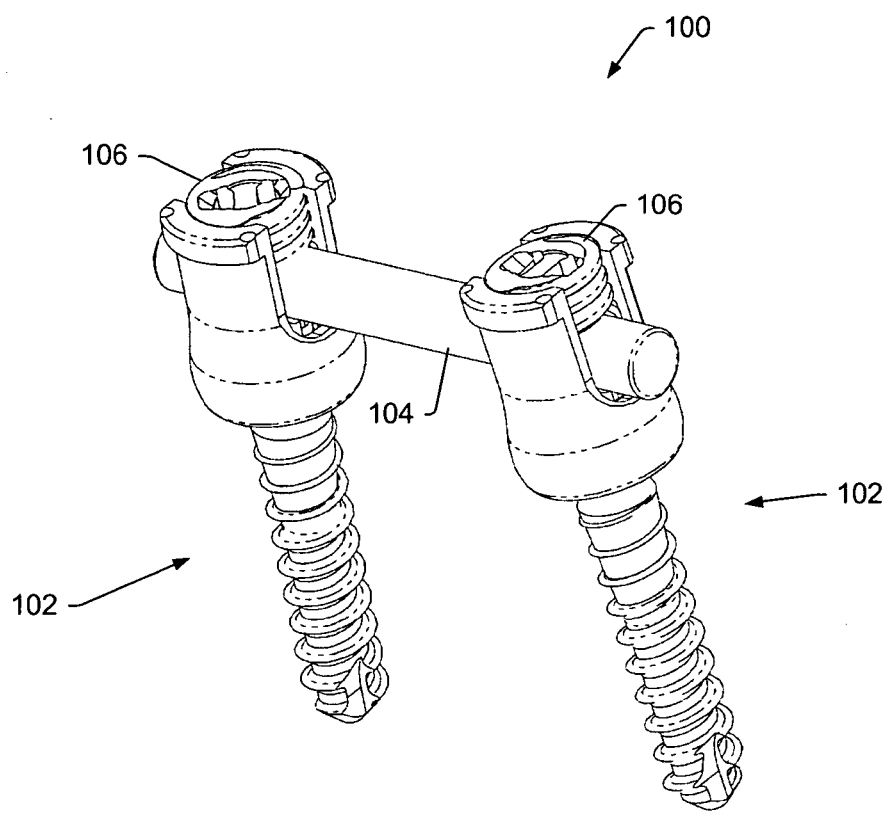
FIG. 1 depicts a perspective view of an embodiment of a spinal stabilization system.

While the invention is susceptible to various modifications and alternative forms, specific embodiments thereof are shown by way of example in the drawings and will herein be described in detail. The drawings may not be to scale. It should be understood that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION

A spinal stabilization system may be installed in a patient to stabilize a portion of a spine. Spinal stabilization may be used, but is not limited to use, in patients having degenerative disc disease, spinal stenosis, spondylolisthesis, pseudoarthrosis, and/or spinal deformities; in patients having fracture or other vertebral trauma; and in patients after tumor resection. A spinal stabilization system may be installed using a minimally invasive procedure. An instrumentation set may include instruments and spinal stabilization system components for forming a spinal stabilization system in a patient and for facilitating compression or distraction of one or more vertebral bodies.

A minimally invasive procedure may be used to limit an amount of trauma to soft tissue surrounding vertebrae that are to be stabilized. In some embodiments, the natural flexibility of skin and soft tissue may be used to limit the length and/or depth of an incision or incisions needed during the stabilization procedure. Minimally invasive procedures may provide limited direct visibility in vivo. Forming a spinal stabilization system using a minimally invasive procedure may include using tools to position system components in the body.

A minimally invasive procedure may be performed after installation of one or more spinal implants in a patient. The spinal implant or spinal implants may be inserted using an anterior procedure and/or a lateral procedure. The patient may be turned and a minimally invasive procedure may be used to install a posterior spinal stabilization system. A minimally invasive procedure for stabilizing the spine may be performed without prior insertion of one or more spinal implants or devices in some patients. In some patients, a minimally invasive procedure may be used to install a spinal stabilization system after one or more spinal implants are inserted using a posterior spinal approach.

A spinal stabilization system may be used to achieve rigid pedicle fixation while minimizing the amount of damage to surrounding tissue. In some embodiments, a spinal stabilization system may be used to provide stability to two adjacent vertebrae (i.e., one vertebral level). A spinal stabilization system may include two bone fastener assemblies. One bone fastener assembly may be positioned in each of the vertebrae to be stabilized. An elongated member may be coupled and secured to the bone fastener assemblies. As used herein, "coupled" components may directly contact each other or may be separated by one or more intervening members. In some embodiments, a single spinal stabilization system may be installed in a patient. Such a system may be referred to as a unilateral, single-level stabilization system or a single-level, two-point stabilization system. In some embodiments, two spinal stabilization systems may be installed in a patient on opposite sides of a spine. Such a system may be referred to as a bilateral, single-level stabilization system or a single-level, four-point stabilization system.

In some embodiments, a spinal stabilization system may provide stability to three or more vertebrae (i.e., two or more vertebral levels). In a two vertebral level spinal stabilization system, the spinal stabilization system may include three bone fastener assemblies. One bone fastener assembly may be positioned in each of the vertebrae to be stabilized. An elongated member may be coupled and secured to the three bone fastener assemblies. In some embodiments, a single two-level spinal stabilization system may be installed in a patient. Such a system may be referred to as a unilateral, two-level stabilization system or a two-level, three-point stabilization system. In some embodiments, two three-point spinal stabilization systems may be installed in a patient on opposite sides of a spine. Such a system may be referred to as a bilateral, two-level stabilization system or a two-level, six-point stabilization system.

In some embodiments, combination systems may be installed. For example, a two-point stabilization system may be installed on one side of a spine, and a three-point stabilization system may be installed on the opposite side of the spine. The composite system may be referred to a five-point stabilization system.

Minimally invasive procedures may reduce trauma to soft tissue surrounding vertebrae that are to be stabilized. Only a small opening may need to be made in a patient. For example, for a single-level stabilization procedure on one side of the spine, the surgical procedure may be performed through a 2 cm to 4 cm incision formed in the skin of the patient. In some embodiments, the incision may be above and between the vertebrae to be stabilized. Dilators, a targeting needle, and/or a tissue wedge may be used to provide access to the vertebrae to be stabilized without the need to form an incision with a scalpel through muscle and other tissue between the vertebrae to be stabilized. A minimally invasive procedure may reduce an amount of postoperative pain felt by a patient as compared to invasive spinal stabilization procedures. A minimally invasive procedure may reduce recovery time for the patient as compared to invasive spinal procedures.

Components of spinal stabilization systems may be made of materials including, but not limited to, titanium, titanium alloys, stainless steel, ceramics, and/or polymers. Some components of a spinal stabilization system may be autoclaved and/or chemically sterilized. Components that may not be autoclaved and/or chemically sterilized may be made of sterile materials. Components made of sterile materials may be placed in working relation to other sterile components during assembly of a spinal stabilization system.

Spinal stabilization systems may be used to correct problems in lumbar, thoracic, and/or cervical portions of a spine. Various embodiments of a spinal stabilization system may be used from the C1 vertebra to the sacrum. For example, a spinal stabilization system may be implanted posterior to the spine to maintain distraction between adjacent vertebral bodies in a lumbar portion of the spine.

FIG. 1 depicts an embodiment of spinal stabilization system 100 that may be implanted using a minimally invasive surgical procedure. Spinal stabilization system 100 may include bone fastener assemblies 102, elongated member 104, and/or closure members 106. Other spinal stabilization system embodiments may include, but are not limited to, plates, dumbbell-shaped members, and/or transverse connectors. FIG. 1 depicts a spinal stabilization system for one vertebral level. In some embodiments, the spinal stabilization system of FIG. 1 may be used as a multi-level spinal stabilization system if one or more vertebrae are located between the vertebrae in which bone fastener assemblies 102 are placed. In other embodiments, multi-level spinal stabilization systems may include additional bone fastener assemblies to couple to one or more other vertebrae.

Figure 2:
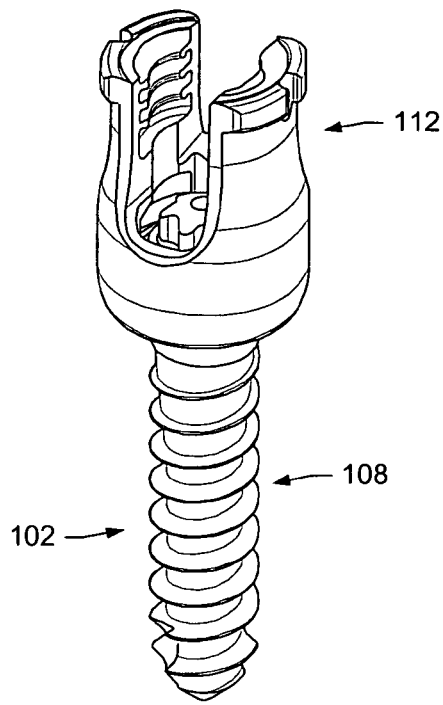
FIG. 2 depicts a perspective view of an embodiment of a bone fastener assembly.
Figure 3:
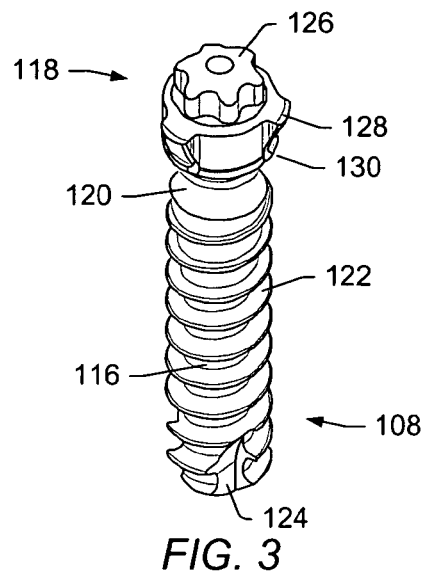
FIG. 3 depicts a perspective view of an embodiment of a bone fastener.
Figure 4:
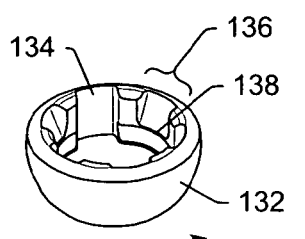
FIG. 4 depicts a perspective view of an embodiment of a bone fastener assembly ring.
Figure 5:
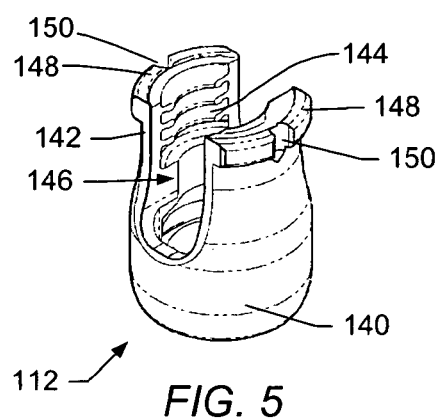
FIG. 5 depicts a perspective view of an embodiment of a bone fastener assembly collar.

FIG. 2 depicts a perspective view of bone fastener assembly 102. FIGS. 3-5 depict embodiments of bone fastener assembly components. Components of bone fastener assembly 102 may include, but are not limited to, bone fastener 108 (shown in FIG. 3), ring 110 (shown in FIG. 4), and collar 112 (shown in FIG. 5). Bone fastener 108 may couple bone fastener assembly 102 to a vertebra. Ring 110 may be positioned between a head of bone fastener 108 and collar 112.

Figure 6:
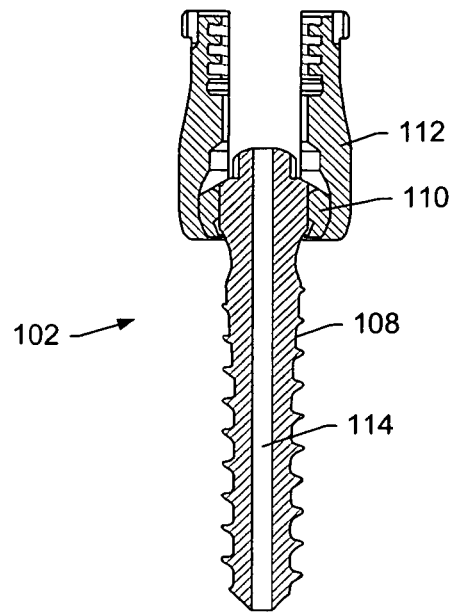
FIG. 6 depicts a cross-sectional view of an embodiment of a bone fastener assembly.

FIG. 6 depicts a cross-sectional representation of bone fastener 108, ring 110, and collar 112 of bone fastener assembly 102. Bone fastener 108 of bone fastener assembly 102 may include passage 114. A guide wire may be placed through passage 114 so that bone fastener 108 may be inserted into a vertebra at a desired location and in a desired angular orientation relative to the vertebra with limited or no visibility of the vertebra.

A bone fastener may be, but is not limited to, a bone screw, a ring shank fastener, a barb, a nail, a brad, or a trocar. Bone fasteners and/or bone fastener assemblies may be provided in various lengths in an instrumentation set to accommodate variability in vertebral bodies. For example, an instrumentation set for stabilizing vertebrae in a lumbar region of the spine may include bone fastener assemblies with lengths ranging from about 30 mm to about 75 mm in 5 mm increments.

FIG. 3 depicts an embodiment of bone fastener 108. Bone fastener 108 may include shank 116, head 118, and neck 120. Shank 116 may include threading 122. In some embodiments, threading 122 may include self-tapping start 124. Self-tapping start 124 may facilitate insertion of bone fastener 108 into vertebral bone.

Head 118 of bone fastener 108 may include various configurations to engage a driver that inserts the bone fastener into a vertebra. In some embodiments, the driver may also be used to remove an installed bone fastener from a vertebra. In some embodiments, head 118 may include one or more tool portions 126. Tool portions 126 may be recesses and/or protrusions designed to engage a portion of the driver.

Head 118 of bone fastener 108 may include one or more splines 128, as depicted in FIG. 3. In some head embodiments, head 118 may include three splines. Splines 128 may be equally spaced circumferentially around head 118 of bone fastener 108. In some head embodiments, splines 128 may be spaced at unequal distances circumferentially around head 118. Splines 128 may include various surface configurations and/or texturing to enhance coupling of bone fastener 108 with a ring of a bone fastener assembly. In some embodiments, sides of the splines may be tapered so that the splines form a dovetail connection with a ring. In some embodiments, spline width may be tapered so that a good interference connection is established when the bone screw is coupled to a ring. Splines 128 may include one or more projections 130 to facilitate coupling bone fastener 108 with an inner surface of a ring. In some embodiments, projections 130 may be positioned on a lower portion of splines 128. In some embodiments, the splines may include recessed surfaces that accept projections extending from surfaces of the ring.

Neck 120 of bone fastener 108 may have a smaller diameter than adjacent portions of head 118 and shank 116. The diameter of neck 120 may fix the maximum angle that the collar of the bone fastener assembly can be rotated relative to bone fastener 108. In some embodiments, neck 120 may be sized to allow up to about 40.degree. or more of angulation of the collar relative to the bone fastener. In some embodiments, the neck may be sized to allow up to about 30.degree. of angulation of the collar relative to the bone fastener. In some embodiments, the neck may be sized to allow up to about 20.degree. of angulation of the collar relative to the bone fastener.

FIG. 4 depicts a perspective view of an embodiment of ring 110. Outer surface 132 of ring 110 may have a contour that substantially complements a contour of an inner surface of a collar in which the ring resides. A contour of the outer surface of the ring may be a spherical portion. When the ring is positioned in the collar, the complementary shape of the ring outer surface and the inner surface of the collar that contacts the ring allows angulation of the collar relative to a bone fastener coupled to the ring. The contour of the outer surface of the ring and the inner surface of the collar may inhibit removal of the ring from the collar after insertion of the ring into the collar.

Outer surface 132 of ring 110 may have a smooth finish. In some embodiments, outer surface 132 may be surface treated or include coatings and/or coverings. Surface treatments, coatings, and/or coverings may be used to adjust frictional and/or wear properties of the outer surface of the ring.

An inner surface of ring 110 may include one or more grooves 134 and/or one or more seats 136. Seats 136 may be circumferentially offset from grooves 134. Grooves 134 may be sized to allow passage of splines of a bone fastener (e.g., splines 128 shown in FIG. 3) through the ring. When the splines are inserted through grooves 134, the bone fastener may be rotated until the splines align with seats 136. The bone fastener may be pulled or driven so that the splines are positioned in seats 136. In some embodiments, projections (e.g., projections 130 in FIG. 3) may pass over ridges 138 of ring 110. Passage of the projections over ridges 138 may securely couple the bone fastener to the ring and inhibit separation of the ring from the bone fastener.

In a ring embodiment, a number of grooves 134 and a number of seats 136 may equal a number of splines 128 on a head of a bone fastener. Seats 136 and grooves 134 may be equally spaced circumferentially around the inner surface of ring 110. In some embodiments, seats 136 may be circumferentially offset about 600 from grooves 134.

As used herein, the term "collar" includes any element that wholly or partially encloses or receives one or more other elements. A collar may enclose or receive elements including, but not limited to, a bone fastener, a closure member, a ring, and/or an elongated member. In some embodiments, a collar may couple two or more other elements together (e.g., an elongated member and a bone fastener). A collar may have any of various physical forms. In some embodiments, a collar may have a "U" shape, however it is to be understood that a collar may also have other shapes.

Collar 112 may include body 140 and arms 142. Arms 142 may extend from body 140. Body 140 of collar 112 may be greater in width than a width across arms 142 of collar 112 (i.e., body 140 may have a maximum effective outer diameter greater than a maximum effective outer diameter of arms 142). A reduced width across arms 142 may allow an extender to be coupled to the arms without substantially increasing a maximum effective outer diameter along a length of collar 112. Thus, a reduced width across arms 142 may reduce bulk at a surgical site.

Inner surfaces of arms 142 may include threading 144. Threading 144 may engage complementary threading of a closure member to secure an elongated member to a bone fastener assembly.

Arms 142 and body 140 may form slot 146. Slot 146 may be sized to receive an elongated member. When an elongated member is positioned in slot 146, a portion of the elongated member may contact a head of a bone fastener positioned in the collar.

Arms 142 may include ridges or flanges 148. Flange 148 may allow collar 112 to be coupled to an extender so that translational motion of the collar relative to the extender is inhibited. Flanges 148 may also include notches 150. A movable member of an extender may extend into notch 150. When the movable member is positioned in notch 150, a channel in the extender may align with a slot in collar 112. With the movable member positioned in notch 150, rotational movement of collar 112 relative to the extender may be inhibited.

A bone fastener may be positioned in a collar such that the bone fastener is able to move radially and/or rotationally relative to the collar (or the collar relative to the bone fastener) within a defined range of motion. Motion of the bone fastener relative to the collar (or the collar relative to the bone fastener) may be referred to as "angulation" and/or "polyaxial movement".

Figure 7:
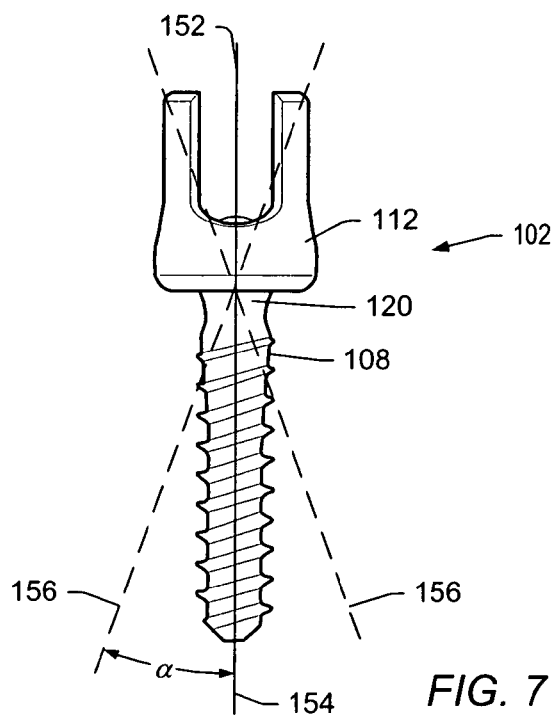
FIG. 7 depicts a front view of an embodiment of a bone fastener assembly with a collar that allows for angulation of a bone fastener relative to the collar in a conical range of motion that is symmetrical relative to an axis that passes through a central axis of the collar and a central axis of a bone fastener.

FIG. 7 depicts bone fastener assembly 102 with central axis 152 of collar 112 aligned with central axis 154 of bone fastener 108. Bone fastener 108 may be angulated in a symmetrical conical range of motion characterized by angle a. about the aligned axes. Bone fastener 108 may be constrained from motion outside of limit axis 156 by contact between neck 120 of bone fastener 108 and collar 112. Alignment of axis 154 of bone fastener 108 with central axis 152 of collar 112 may be considered a neutral position relative to the range of motion. The alignment is a neutral position because bone fastener 108 may be angulated an equal amount in any direction from central axis 152. When a driver is coupled to bone fastener 108, axis 154 of bone fastener 108 may be substantially aligned with axis 152 of collar 112 to facilitate insertion of the bone fastener into a vertebral body.

Figure 8:
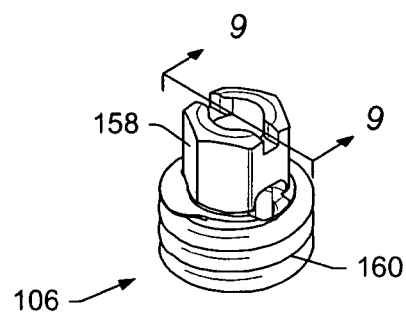
FIG. 8 depicts a perspective view of an embodiment of a closure member.

A closure member may be coupled to a collar of a bone fastener assembly to fix an elongated member positioned in the collar to the bone fastener assembly. FIG. 1 depicts closure members 106 coupled to bone fastener assemblies 102. FIG. 8 depicts closure member 106 prior to insertion of the closure member into a collar of a bone fastener assembly. Closure member 106 may include tool portion 158 and male threading 160. Tool portion 158 may couple to a tool that allows closure member 106 to be positioned in a collar. Tool portion 158 may include various configurations (e.g., threads, hexalobular connections, hexes) for engaging a tool (e.g., a driver). Male threading 160 may have a shape that complements the shape of female threading in arms of a collar (e.g., threading 144 depicted in FIG. 5).

Figure 9:
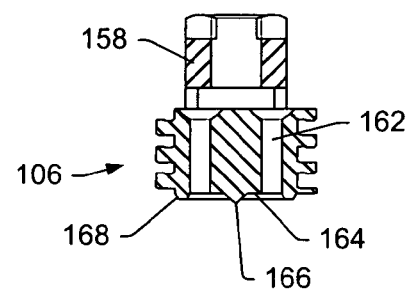
FIG. 9 depicts a cross-sectional representation of the closure member taken substantially along plane 9-9 indicated in FIG. 8.

FIG. 9 depicts a cross-sectional representation of closure member 106 taken substantially along plane 9-9 of FIG. 8. Closure member 106 may include removal openings 162. A drive tool may be inserted into removal openings 162 to allow removal of closure member 106 after tool portion 158 has been sheared off. Removal openings 162 may include any of a variety of features including, but not limited to, sockets, holes, slots, and/or combinations thereof. In an embodiment, removal openings 162 are holes that pass through bottom surface 164 of closure member 106.

A bottom surface of a closure member may include structure and/or texturing that promotes contact between the closure member and an elongated member. A portion of the structure and/or texturing may enter and/or deform an elongated member when the closure member is coupled to the elongated member. Having a portion of the closure member enter and/or deform the elongated member may couple the elongated member to the closure member and a bone fastener assembly so that movement of the elongated member relative to the bone fastener assembly is inhibited. In a closure member embodiment, such as the embodiment depicted in FIG. 9, bottom surface 164 of closure member 106 may include point 166 and rim 168. In some embodiments, rim 168 may come to a sharp point. In some embodiments, a height of rim 168 may be less than a height of point 166. In other embodiments, a height of rim 168 may be the same or larger than a height of point 166. In some embodiments, rim 168 may not extend completely around the closure member. For example, eight or more portions of rim 168 may be equally spaced circumferentially around closure member 106. In certain embodiments, a solid central core including point 166 and rim 168 may enhance the ability of closure member 106 to secure an elongated member in a collar.

Figure 10:
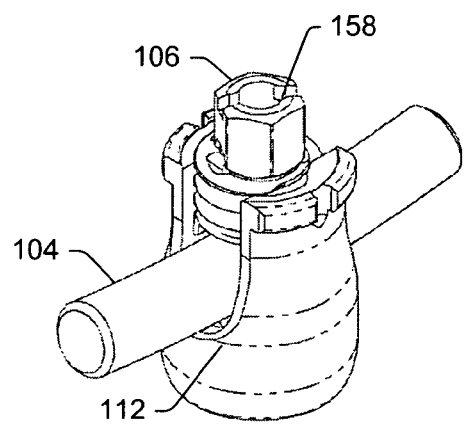
FIG. 10 depicts a perspective view of an embodiment of a portion of a spinal stabilization system.

FIG. 10 depicts a portion of a spinal stabilization system with closure member 106 coupled to collar 112 before tool portion 158 is sheared off. Closure member 106 may couple to collar 112 by a variety of systems including, but not limited to, standard threads, modified threads, reverse angle threads, buttress threads, or helical flanges. Closure member 106 may be advanced into an opening in a collar to engage a portion of elongated member 104. In some embodiments, closure member 106 may inhibit movement of elongated member 104 relative to collar 112.

Various instruments may be used in a minimally invasive procedure to form a spinal stabilization system in a patient. The instruments may include, but are not limited to, positioning needles, guide wires, dilators, bone awls, bone taps, sleeves, extenders, drivers, tissue wedges, elongated member length estimating tools, mallets, tissue retractors, and tissue dilators. The instruments may be provided in an instrumentation set. The instrumentation set may also include components of the spinal stabilization system: The components of the spinal stabilization system may include, but are not limited to, bone fastener assemblies of various sizes and/or lengths, elongated members, and closure members.

Instruments used to install a spinal stabilization system may be made of materials including, but not limited to, stainless steel, titanium, titanium alloys, ceramics, and/or polymers. Some instruments may be autoclaved and/or chemically sterilized. Some instruments may be, or may include, components that cannot be autoclaved or chemically sterilized. Instruments or components of instruments that cannot be autoclaved or chemically sterilized may be made of sterile materials.

An extender may be used as a guide to install bone fasteners of a bone fastener assembly in vertebral bone. An extender may be coupled to a collar of a bone fastener assembly. A distal end of an extender may be tapered or angled to reduce bulk at a surgical site. Instruments may be inserted into the extender to manipulate the bone fastener assembly. Movement of the extender may alter an orientation of a collar relative to a bone fastener of the bone fastener assembly. In some embodiments, an extender may be used as a retractor during a spinal stabilization procedure.

An extender for a single-level vertebral stabilization system may include one or more channels in a wall of the extender to allow access to an adjacent vertebra. For some single-level vertebral stabilization procedures, only single-channel extenders (i.e., extenders with a single channel in a wall of the extender) may be used. For other single-level vertebral stabilization procedures, one or more multi-channel extenders (i.e., extenders with two or more channels in a wall of the extender) may be used. Channels may provide flexibility to or enhance flexibility of a multi-channel extender. In some embodiments, a proximal portion of a multi-channel extender may have a solid circumference. A region of solid circumference in a multi-channel extender 16 may enhance stability of the multi-channel extender. In some embodiments, a multi-channel extender may be longer than a single-channel extender.

An extender used at a middle vertebra in a multi-level stabilization procedure may be a multi-channel extender. Channels in a multi-channel extender may allow access to adjacent vertebrae from a middle vertebra. An extender used at an end vertebra of a multi-level stabilization system may be a single-channel extender or a multi-channel extender. A system for coupling a bone fastener assembly to a multi-channel extender may include a limiter that inhibits spreading of anus of the extender to inhibit release of the bone fastener assembly from the extender.

Instruments may access a bone fastener assembly through a passage in an extender. In some embodiments, a channel in a wall of an extender may extend a full length of the extender. In some embodiments, especially in embodiments of multi-channel extenders, a channel in a wall of an extender may extend only a portion of the length of the extender. A channel may extend to a distal end of an extender such that an elongated member inserted in the channel may pass from the extender into a slot of a collar of a bone fastener assembly coupled to the extender.

A channel in an extender may be any of a variety of shapes. A channel may have a width that exceeds a width (e.g., a diameter) of an elongated member that is to be inserted in the channel. In some embodiments, a channel may be a linear opening parallel to a longitudinal axis of the extender.

Movable members may extend through portions of an extender proximate a channel in the extender. Movable members may engage notches in a collar to establish a radial orientation of the extender on the collar and/or to inhibit rotation of the collar relative to the extender. In some embodiments, a distal end of a movable member may be a projection that engages an opening in a collar. In certain embodiments, a proximal end of a movable member may include a tool portion. The tool portion may facilitate engaging the collar with the extender.

Figure 11:
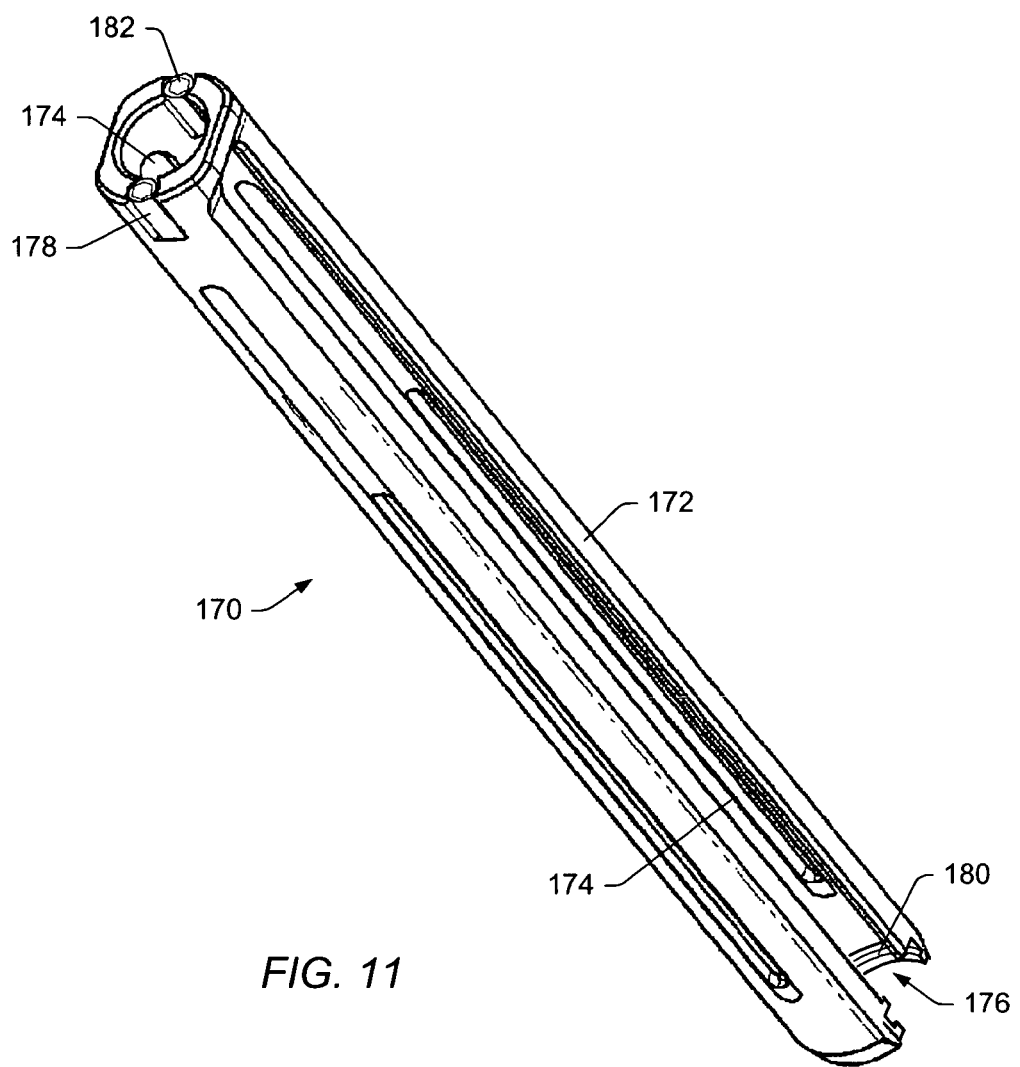
FIG. 11 depicts a perspective view of an embodiment of a multi-channel extender.

FIG. 11 depicts an embodiment of extender 170. Extender 170 may be a multi-channel extender. Extender 170 may include wall 172, channels 174, passage 176, movable members 178, and flange 180. Channels 174 may extend from a distal end of extender 170 through a portion of wall 172. Channels 174 may allow instruments to be positioned and used to form a plane through soft tissue to one or more adjacent vertebrae. An elongated member may be inserted in the tissue plane and positioned in collars of bone fastener assemblies anchored in vertebrae and coupled to extenders. Passage 176 may allow instruments to be positioned and used to manipulate a bone fastener assembly that is coupled to a distal end of extender 170. Movable members 178 may be part of a system that couples a bone fastener assembly to extender 170. In some embodiments, movable members 178 may include tool portion 182. A driver may be positioned in tool portion 182. The driver (e.g., a hex wrench) may be used to extend or retract a distal end of movable member 178. A distal end of extender 170 may include flange 180 that mates with a complementary flange on a collar of a bone fastener assembly. A distal end of extender 170 may be tapered to reduce bulk (e.g., reduce spin diameter) at a surgical site.

FIG. 12 depicts a top view of an embodiment of extender 170 coupled to a bone fastener assembly. Tool portion 126 of bone fastener 108 is a hexalobular connection.

FIG. 13 depicts a cross-sectional representation of a portion of extender 170 with bone fastener assembly 102 taken substantially along line 13-13 of FIG. 12. Flange 180 of extender 170 may mate with flange 148 of collar 112 to inhibit translation of the extender relative to the collar. Extender 170 may also include stop 184. Stop 184 may engage a portion of collar 112 to inhibit separation of walls 172. During use, stop 184 may inhibit undesired separation of bone fastener assembly 102 from extender 170.

FIG. 14 depicts a cross-sectional representation of a portion of extender 170 with bone fastener assembly 102 and elongated member 104 taken substantially along line 14-14 of FIG. 12. Distal ends of movable members 178 may extend into notches (e.g., notches 150 depicted in FIG. 5) in collar 112. Portions of walls 172 of extender 170 may include threading. Portions of movable members 178 may include threading complementary to threaded portions of walls 172. Threading of movable members 178 may engage threading in walls 172 such that rotation of the movable members advances or retracts the movable members relative to the walls.

As shown in FIG. 14, collar 112 may be designed such that elongated member 104 lies below a distal end of extender 170. Coupling extender 170 to collar 112 above elongated member 104 may reduce bulk at a surgical site. With elongated member 104 coupled to collar 112 below a distal end of extender 170, the extender may be removed without interference from the elongated member of a spinal stabilization system.

Figure 15:
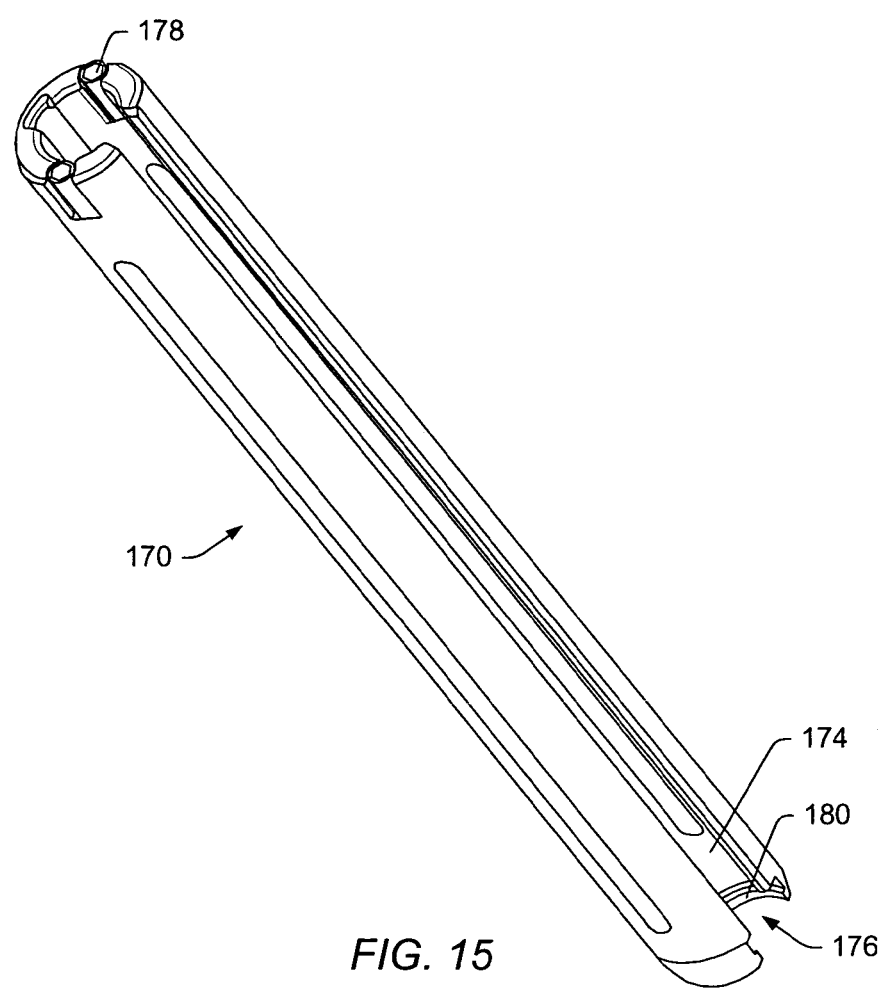
FIG. 15 depicts a perspective view of an embodiment of a single-channel extender.

FIG. 15 depicts an embodiment of extender 170. Extender 170 may be a single-channel extender for use in single-level or multi-level spinal stabilization procedures. Extender 170 may be used at the outermost vertebrae to be stabilized during installation of a multi-level vertebral stabilization system. Extender 170 may be coupled to a collar of a bone fastener assembly with movable members 178 and/or flange 180. Instruments may be inserted through passage 176 of extender 170 to access an anchored bone fastener assembly coupled to the extender. An instrument may be moved through channel 174 toward an adjacent vertebra to form a tissue plane in soft tissue between extender 170 and the adjacent vertebra.

An extender may be coupled to a collar of a bone fastener assembly in various ways. When an extender is coupled to a collar, rotation and translation of the extender relative to the collar may be inhibited. A system used to couple an extender and collar should be simple, inexpensive to implement, and should not significantly weaken the mechanical strength of the collar and/or the extender. Extenders may be coupled to collars using various coupling systems including, but not limited to, flanges, threaded connections, interlocking connections (e.g., ratcheting connection systems), and/or interference fits.

Extenders may be of various lengths. Extenders of different lengths may be used in the same surgical procedure. An extender length used in a spinal stabilization procedure may be determined by a patient's anatomy. Extenders may be just short enough to allow manipulation by a medical practitioner above an incision in a patient. A multi-channel extender may be longer than a single-channel extender.

Figure 16:
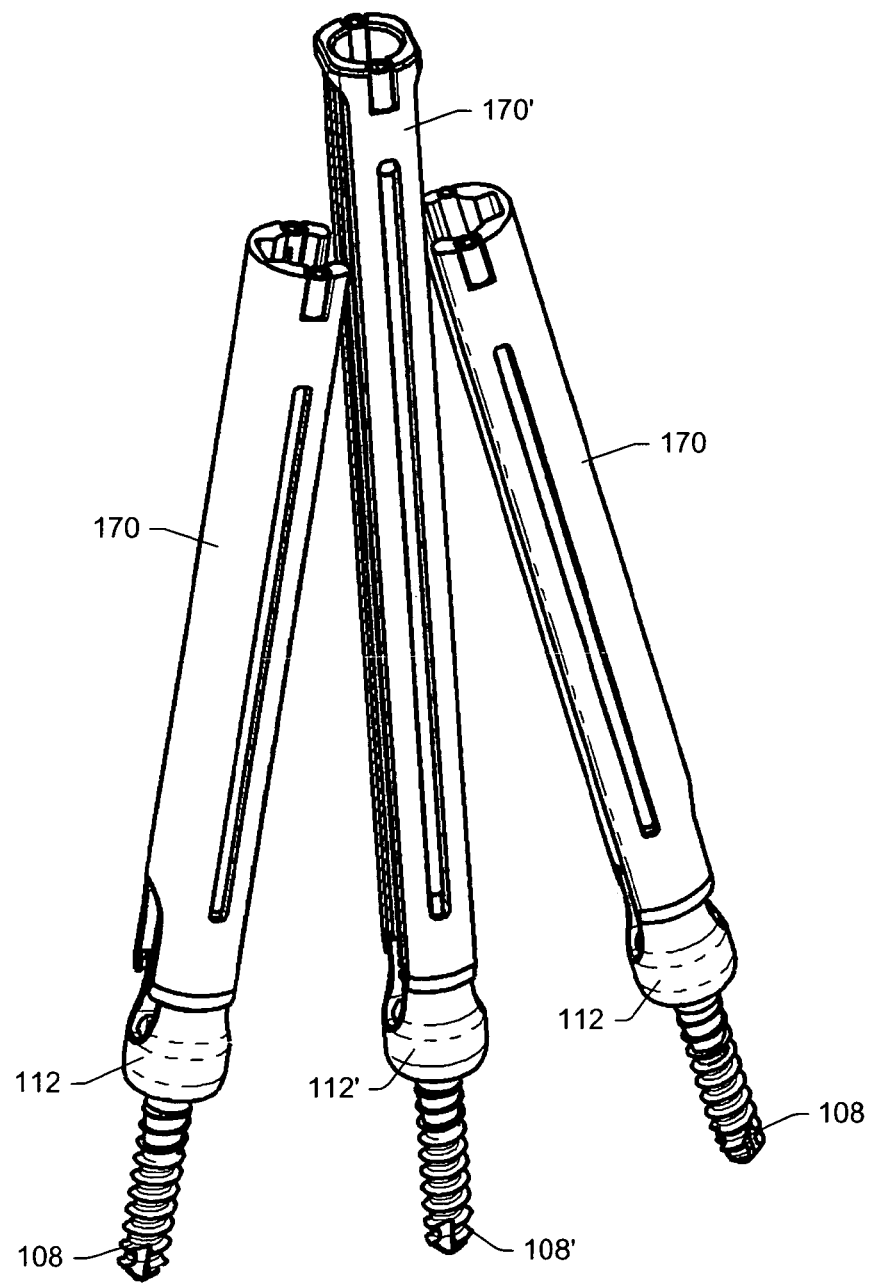
FIG. 16 depicts a perspective view of an embodiment of extenders coupled to bone fastener assemblies.

When bone fasteners of poly axial bone fastener assemblies are positioned in vertebral bone, extenders coupled to collars of the bone fastener assemblies may be moved in desired positions. During surgery, an extender in a patient may be oriented towards an adjacent vertebra that is to be stabilized to reduce the required incision size. In some embodiments, channels of the extenders may be aligned so that an elongated member may be positioned in collars of the bone fastener assemblies. FIG. 16 depicts an orientation of three extenders. Extenders 170, 170' may couple to collars 112, 112'. Bone fasteners 108, 108' may be inserted into vertebrae. Single-channel extenders 170 may be coupled to collars 112 before insertion of bone fasteners 108 into two outer pedicles to be stabilized. Multi-channel extender 170' may be coupled to collar 112' before insertion of bone fastener 108' into a central pedicle of the three adjacent pedicles. Single-channel extenders 170 may be angled towards multi-channel extender 170'. Channels of the extenders may be aligned so that an elongated member may be moved down the extenders and into collars of the bone fastener assemblies.

After a bone fastener assembly is coupled to an extender, a driver may be coupled to a bone fastener of the bone fastener assembly. The driver may be used to insert the bone fastener into vertebral bone.

After bone fastener assemblies are installed and an elongated member is placed in the bone fastener assemblies, closure members may be secured to the bone fastener assemblies. When a closure member is threaded on a bone fastener assembly, a counter torque wrench may be used to inhibit the application of torque to the spine of the patient. A counter torque wrench may hold an extender that is coupled to a collar as the tool portion of a closure member is sheared off. In certain embodiments, about 90 in-lbs of torque may be required to shear off the tool portion of a closure member.

During some spinal stabilization procedures, an instrument may be used to adjust a separation distance between vertebrae. The instrument may be an adjuster. An adjuster is any instrument used to change the separation distance between vertebral bodies, hold the vertebral bodies at a desired separation distance, and allow the vertebral bodies to be at least temporarily secured to maintain the separation distance. An adjuster may couple to extenders that are connected to a spinal stabilization system. The spinal stabilization system may be a single-level or a multi-level spinal stabilization system. Establishing a desired separation distance with the adjuster may be achieved, but is not limited to being achieved, by the use of threading, cams, linkage arms, levers, or combinations thereof. In some adjuster embodiments, the adjuster may be a compressor that reduces a distance between vertebrae. In some embodiments, the adjuster may be a distractor that increases a distance between vertebrae. Some adjuster embodiments may be able to reduce a distance between vertebrae, as well as being able to increase a distance between vertebrae.

During some spinal stabilization procedures, an adjuster may be used to translate a first vertebral body toward an adjacent vertebral body to compress the vertebrae. Compression may be performed for many reasons. For example, compression of a vertebra toward an adjacent vertebra may add a compressive load to a fusion device between the vertebrae to reduce the risk of expulsion of the device and/or to increase the rate of bone fusion. The adjuster may translate a first vertebra towards a second vertebra to achieve compression. Compression may include translating one bone fastener assembly along an elongated member of a spinal stabilization system toward another bone fastener assembly of the spinal stabilization system. A final position of the compressed vertebrae may be maintained by securing the elongated member in a collar of the translated bone fastener assembly with a closure member.

During some spinal stabilization procedures, an adjuster may be used to increase a separation distance between a first vertebral body and a second vertebral body to distract the vertebrae. Distraction may be performed for many reasons. For example, a first vertebra may be separated from a second vertebra to establish a desired separation distance between the vertebrae. The adjuster may translate the first vertebra away from the second vertebra to achieve distraction. Distraction may include translating one bone fastener assembly along an elongated member of a spinal stabilization system away from another bone fastener assembly of the spinal stabilization system. A final position of the distracted vertebrae may be maintained by securing the elongated member in a collar of the translated bone fastener assembly with a closure member.

Figure 17:
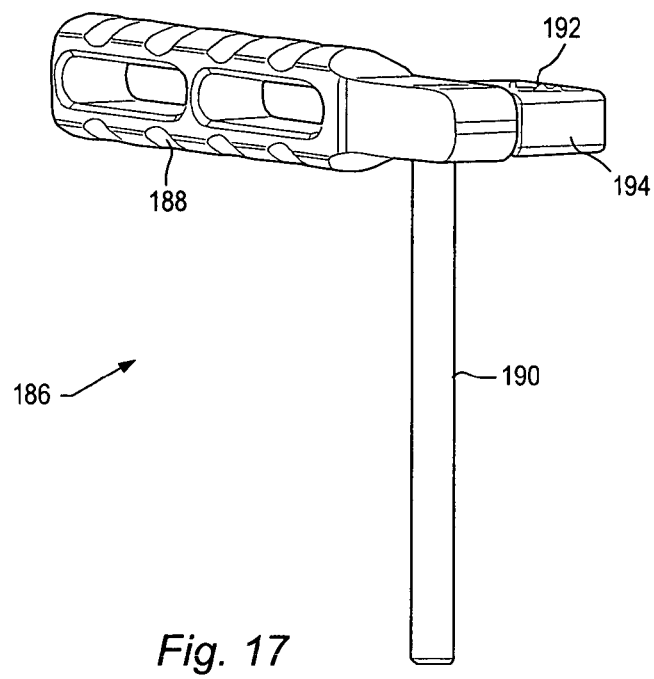
FIG. 17 depicts a perspective view of an embodiment of an adjuster.
Figure 18:
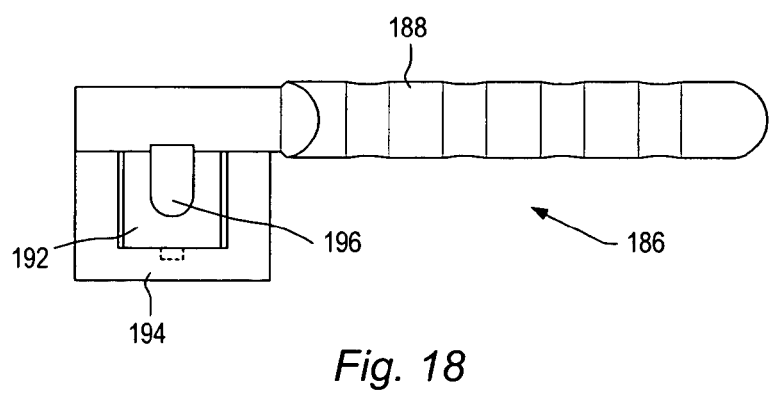
FIG. 18 depicts a top view representation of an embodiment of an adjuster.

FIG. 17 depicts a perspective view of an embodiment of an adjuster designed to pivot above a surface of the skin during use. FIG. 18 depicts a top view of the adjuster embodiment depicted in FIG. 17. Adjuster 186 may include handle 188, shaft 190, pivot 192 and pivot holder 194. Shaft 190 may be coupled to handle knob 188. Pivot 192 may be free to rotate in holder 194. Opening 196 in pivot 192 may be sized to accept a shaft of a driver for a closure member.

Prior to use of the adjuster embodiment depicted in FIG. 17, a closure member may be coupled to a collar of a first bone fastener assembly positioned in a first vertebra. A driver may be used to tighten the closure member so that movement of an elongated member positioned in the collar is inhibited. A closure member may be coupled to a collar of a second bone fastener assembly that is positioned in a second vertebra. The collar in the second bone fastener assembly may be tightened with the driver until the closure member contacts the elongated member. Then, the closure member may be backed off from 0.5 to 2.5 turns so that the collar of the second bone fastener assembly can be translated relative to the elongated member.

Figure 19:
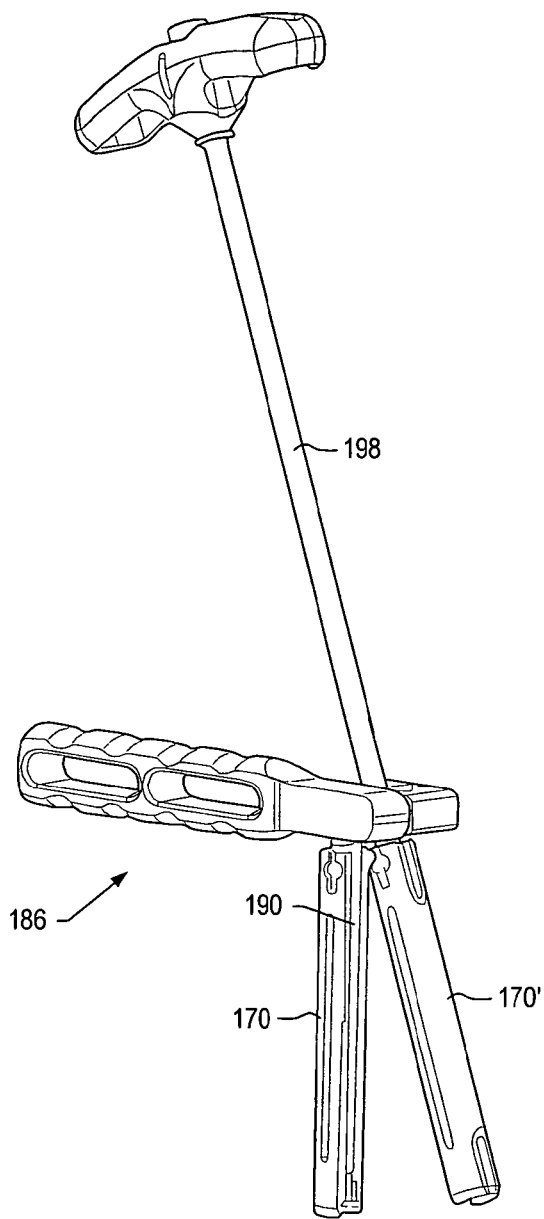
FIG. 19 depicts an embodiment of the adjuster shown in FIG. 17 with a driver inserted through an opening in the adjuster.

The shaft of the driver may be positioned in the opening 196 of adjuster 186. Shaft 190 of adjuster 186 may be positioned in an extender coupled to the collar of the first bone fastener assembly. FIG. 19 depicts shaft 190 of adjuster 186 positioned in extender 170. The diameter of the shaft is sized to prevent the shaft from exiting a channel in extender 170. The shaft of driver 198 may be inserted in extender 170' that is coupled to the collar of the second bone fastener assembly. The shaft of driver 198 may have a diameter that prevents the shaft from exiting a channel in extender 170'. In some embodiments, driver 198 may be rotated about the pivot of adjuster 186 to move the vertebra coupled to the second bone fastener assembly towards the vertebra coupled to the first bone fastener assembly to achieve compression. In some embodiments, driver 198 may be rotated about the pivot of adjuster 186 to move the vertebra coupled to the second bone fastener assembly away from the vertebra coupled to the first bone fastener assembly to achieve distraction. When a desired amount of compression or distraction is achieved, driver 198 may be used to tighten the closure member in the second bone fastener assembly to fix the position of the second bone fastener assembly relative to the elongated member.

In some embodiments, a pivot of the adjuster may not be offset to the side of a shaft of the adjuster. A pivot of the adjuster may be located in front of the shaft. Walls of the handle adjacent to the pivot may be tapered or recessed to allow a shaft of a driver positioned in the pivot to rotate in a desired working range.

Figure 20:
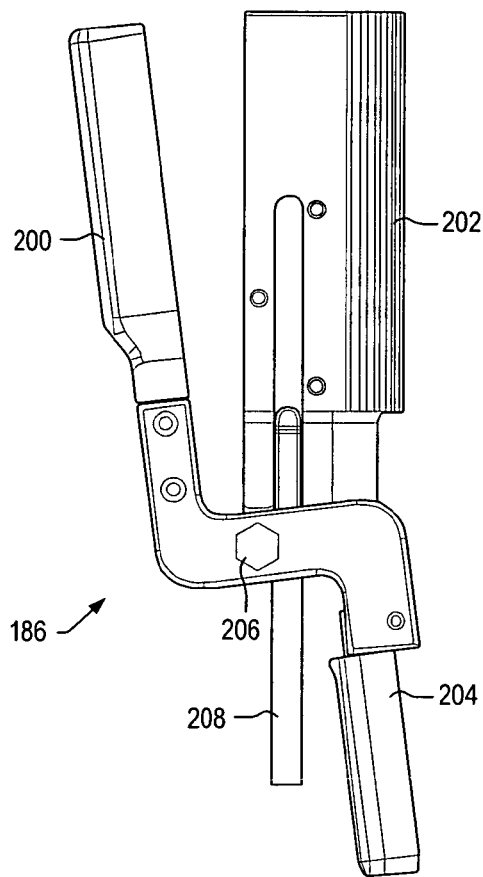
FIG. 20 depicts a side view of an embodiment of an adjuster.

FIG. 20 depicts an adjuster embodiment that may be used as a compressor. Adjuster 186 may be designed such that forces applied to the extenders and the vertebrae are substantially directly opposed to each other during use (e.g., the extenders are in line during compression or distraction). Adjuster 186 may include handles 200, 202. Outer sleeve 204 coupled to handle 200 may provide an opening for a driver to access a closure member positioned in a first extender coupled to a collar of a spinal stabilization system. A portion of handle 202 may fit in a portion of handle 200. In some embodiments, handle 202 may move (e.g., pivot, translate) relative to handle 200 about member 206.

Figure 21:
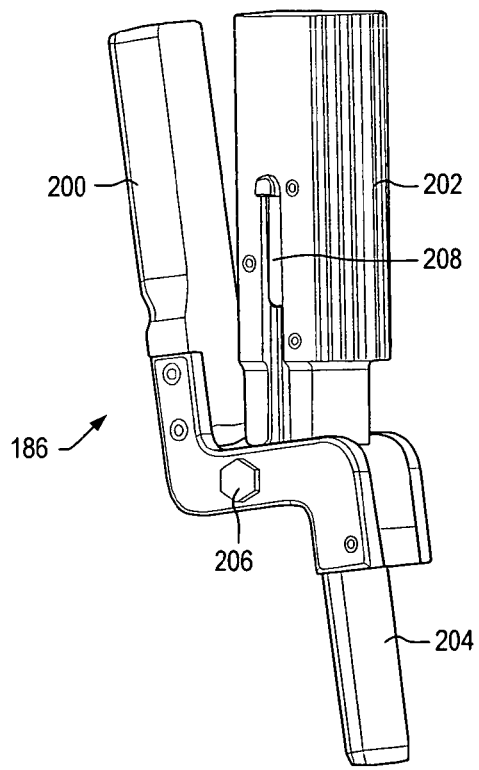
FIG. 21 depicts a perspective view of the embodiment of the adjuster shown in FIG. 20.
Figure 22:
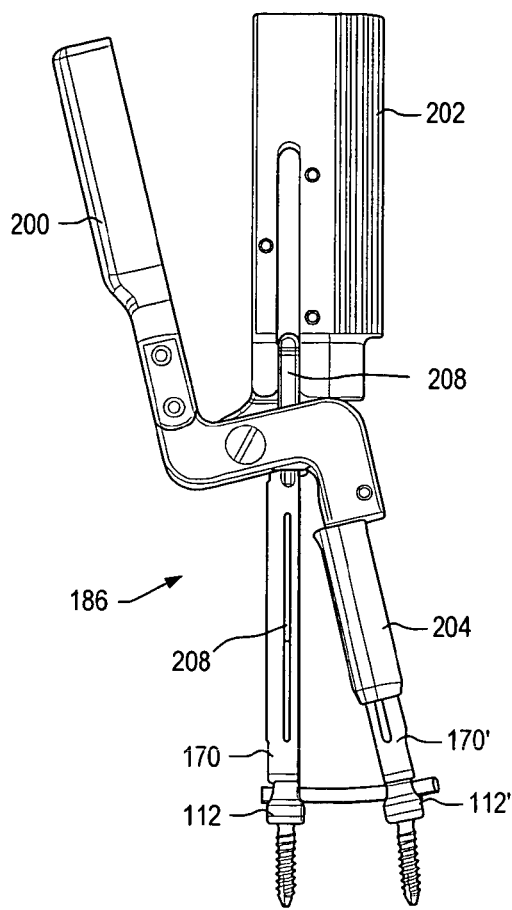
FIG. 22 depicts a side view of an embodiment of an adjuster coupled to extenders that are coupled to a spinal stabilization system
Figure 23:
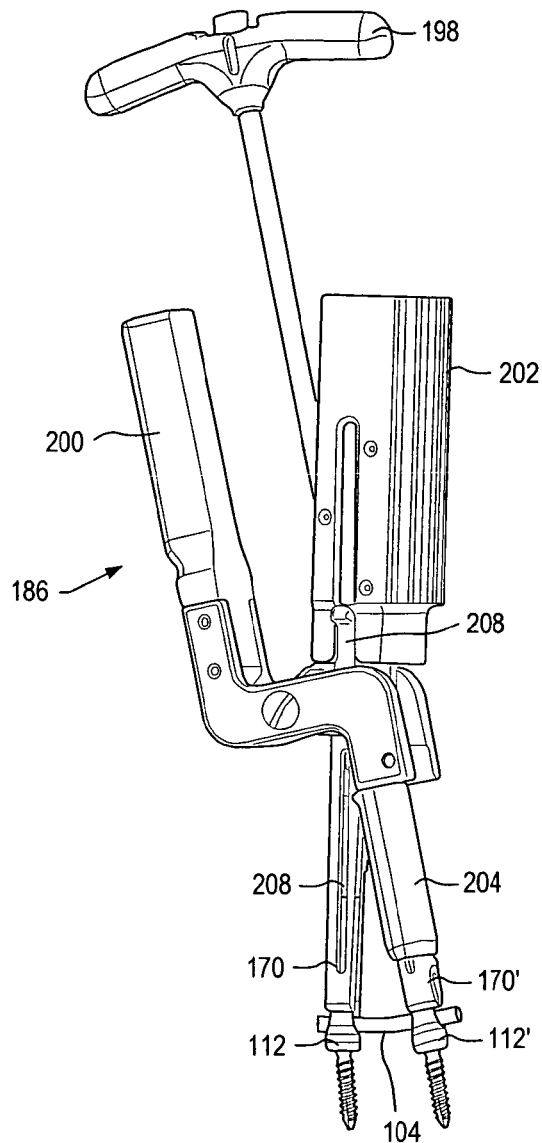
FIG. 23 depicts a perspective view of the adjuster shown in FIG. 22 with a driver inserted through one of the handles of the adjuster.

Outer sleeve 204 of handle 200 may be positioned over an extender coupled to a spinal stabilization system. With outer sleeve 204 positioned over an extender coupled to a spinal stabilization system, sliding shaft 208 may be retracted into handle 202. FIG. 21 depicts sliding shaft 208 retracted into handle 202 of adjuster 186. Handle 202 may pivot about and/or translate relative to member 206 such that sliding shaft 208 may be adjustably positioned in a second extender coupled to the spinal stabilization system. With handle 202 positioned such that sliding shaft 208 is aligned above extender 170, the sliding shaft may be inserted in the extender. FIG. 22 depicts adjuster 186 with sliding shaft 208 positioned in extender 170. With sliding shaft 208 positioned in extender 170 and extender 170' positioned in outer sleeve 204, handles 200, 202 may be compressed. Compressing handles 200, 202 may translate collar 112' toward collar 112 along elongated member 104. Driver 198, depicted in FIG. 23, may be used to tighten a closure member to collar 112' to secure the spinal stabilization system in the desired compressed configuration.

Figure 24:
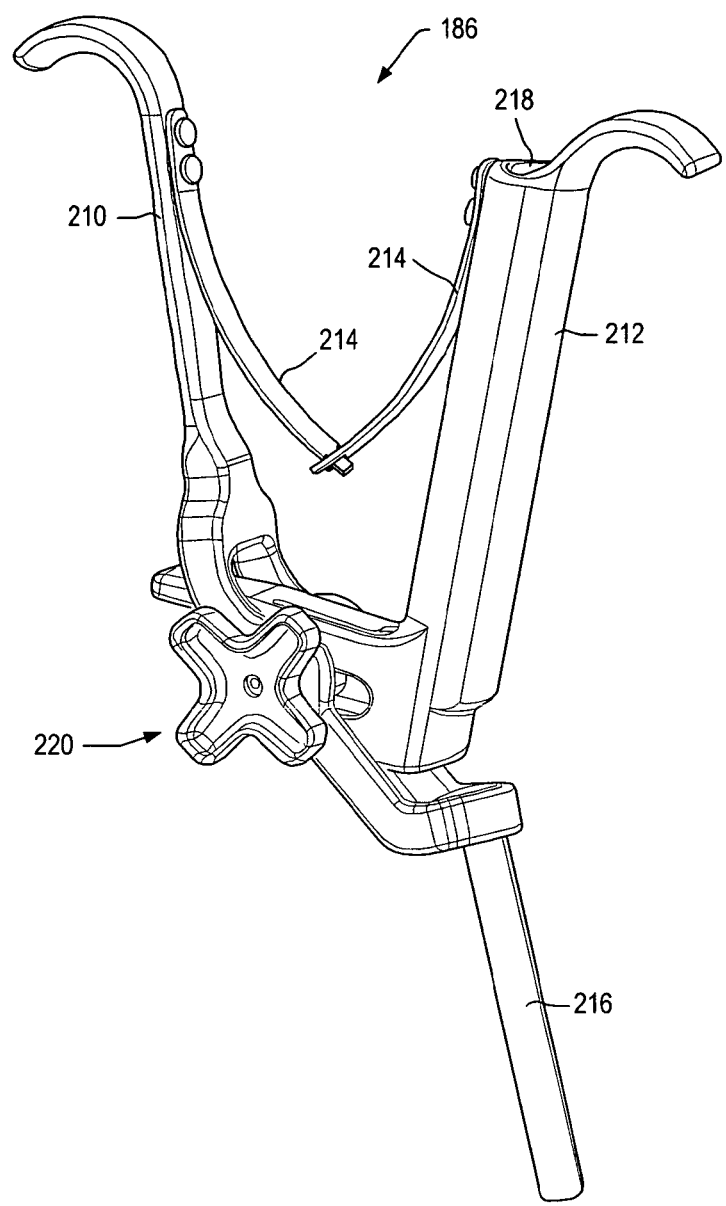
FIG. 24 depicts a perspective view of an embodiment of an adjuster.

FIG. 24 depicts an embodiment of adjuster 186 that may be used as a compressor. In some embodiments, adjuster 186 may include an adjustable pivot axis. Adjuster 186 may include handles 210, 212. Adjuster 186 may include a bias system. In some embodiments, the bias system includes tension members 214 coupled to handles 210, 212. Tension members 214 may provide a force to handles 210, 212 that separates the handles. Handle 210 may align with handle 212 so that forces applied to the handles are directly opposed, thus eliminating or substantially eliminating torsional forces during use. Handle 210 may be coupled to an extender engager. In some embodiments, the extender engager may be shaft 216. In some embodiments, the extender engager may be a hollow shaft that fits over an extender. Shaft 216 may be positioned in a first extender that is coupled to a first collar secured to an elongated member of a spinal stabilization system.

Handle 212 may include a driver engager. The driver engager may couple a closure member driver to the adjuster. A portion of the closure member driver may be inserted in a second extender that is secured to a second collar when an extender engager of the adjuster is coupled to a first extender that is secured to a first collar. In some embodiments, the driver engager may be one or more rings coupled to handle 212 into which the driver is inserted. In an embodiment, the driver engager may be passage 218. A closure member may be coupled to the closure member driver. The closure member may be inserted through passage 218 into the second extender. The closure member may be coupled to the second collar. In some embodiments, the closure member driver may be affixed to the adjuster so that separation of the driver from the adjuster is inhibited.

In some adjuster embodiments, handles 210, 212 of adjuster 186 may be able to translate towards each other. Translation may be allowed or inhibited by engagement mechanism 220. When engagement mechanism 220 allows for translation, the position of handle 212 may be adjusted relative to the position of handle 210. The ability of handle 212 to translate towards handle 210 may facilitate insertion of the adjuster and a shaft of a driver coupled to the adjuster into extenders that are secured to collars of a spinal stabilization system.

Figure 25:
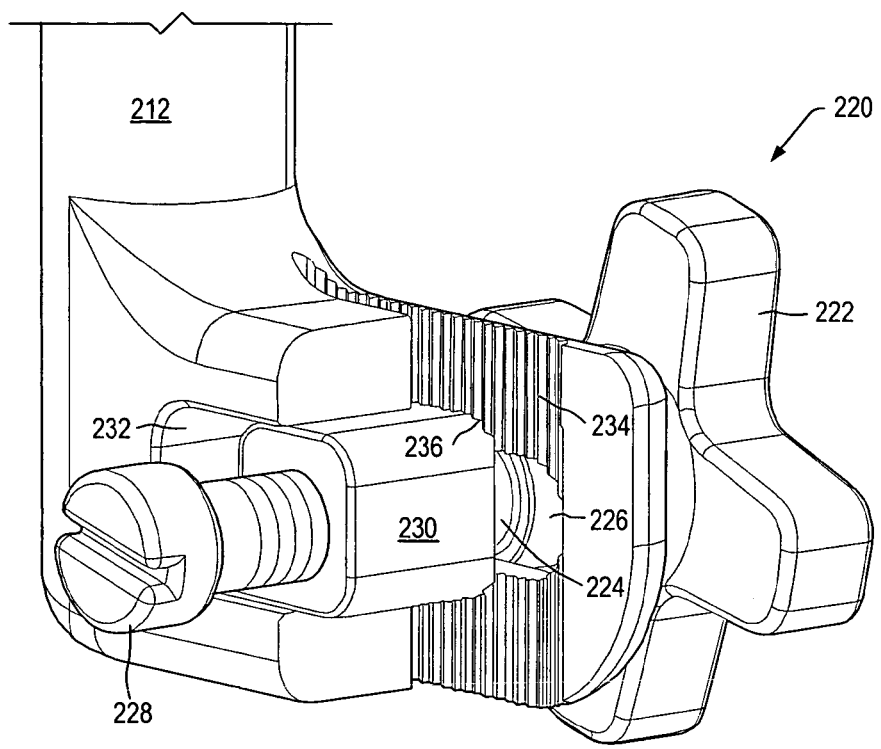
FIG. 25 depicts a cutaway view of an embodiment of an engagement mechanism for the adjusters shown in FIG. 24 and FIG. 28.

FIG. 25 depicts a partial cut-away view of engagement mechanism 220 with handle 212. For clarity, handle 210 is not depicted in FIG. 25. Engagement mechanism 220 may include knob 222. Knob 222 may be coupled to shaft 224. Shaft 224 may be positioned through opening 226 in handle 212. A portion of shaft 224 may be threaded. In some embodiments, end member 228 may be coupled to shaft 224. In some embodiments, movable member 230 may be positioned on shaft 224 between end member 228 and knob 222. End member 228 may inhibit removal of movable member 230, shaft 224, and knob 222 from the adjuster. Movable member 230 may have threading that mates with threading of shaft 224. Movable member 230 may be complementary to a portion of opening 232 in handle 212 to inhibit rotation of the movable member relative to knob 222. In some embodiments, rotation of knob 222 in a first direction may draw movable member 230 toward protrusions 234 on handle 212. Protrusions 236 on movable member 230 may engage (e.g., mate or interlock with) protrusions 234 in handle 212 as knob 222 is rotated. Tightening knob 222 may inhibit translation of handle 210 with respect to handle 212, thus fixing a position of a pivot axis for handles 210, 212.

Figure 26:
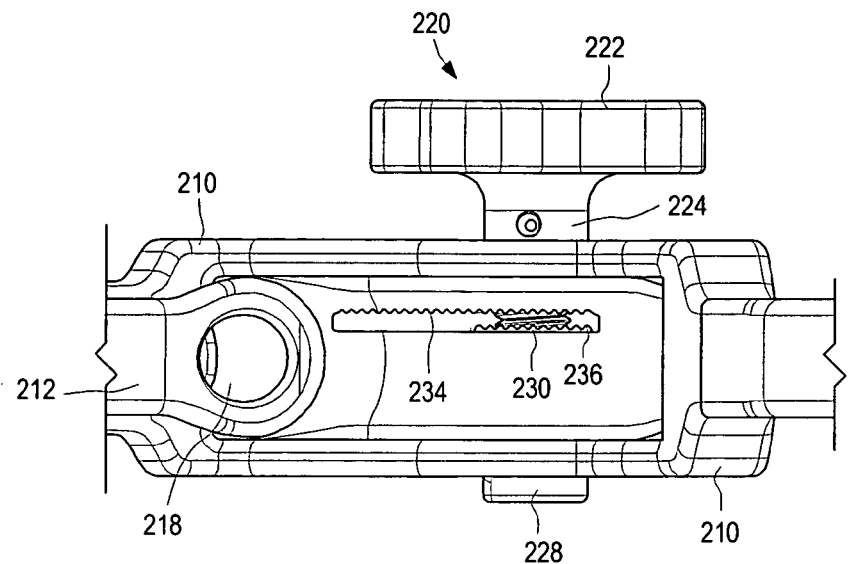
FIG. 26 depicts a top, cutaway view of a portion of the adjusters shown in FIG. 24 and FIG. 28.
Figure 27:
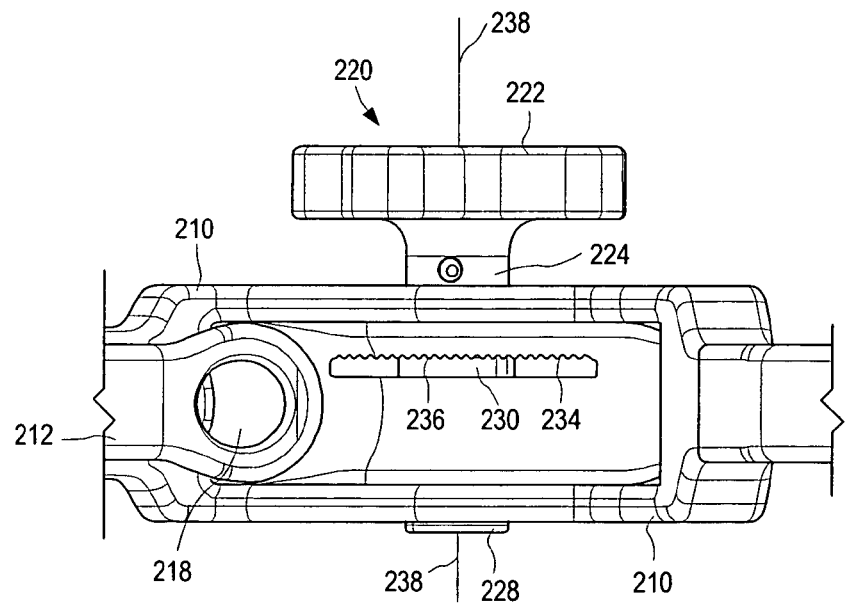
FIG. 27 depicts a top cutaway view of a portion of the adjusters shown in FIG. 24 and FIG. 28.

FIGS. 26 and 27 depict partial top views of engagement mechanism 220 (with the bias system not shown). As depicted in FIGS. 26 and 27, shaft 224 of engagement mechanism 220 may extend from knob 222 through a first opening in handle 210, through an opening in handle 212, and through a second opening in handle 210. Handle 210 is able to pivot relative to shaft 224 about pivot axis 238 (depicted in FIG. 27) of the shaft. End member 228 may be coupled to shaft 224 to inhibit removal of engagement mechanism 220 from openings in handles 210, 212 during use.

FIG. 26 depicts protrusions 234 on handle 212 and protrusions 236 on movable member 230 in an unengaged position. With protrusions 234, 236 unengaged, shaft 224 and handle 210 may be translated in openings 226, 232 (depicted in FIG. 25) towards or away from passage 218 in handle 212. Translating shaft 224 may allow a user to adjust a position about which handle 210 will pivot relative to handle 212. Translating shaft 224 may facilitate coupling the adjuster and a closure member driver coupled to the adjuster to extenders that are secured to a spinal stabilization system.

When a desired relative position of handles 210, 212 has been established, engagement mechanism 220 may be activated (e.g., knob 222 may be tightened) to inhibit relative translation of the handles and to fix a position of pivot axis 238 relative to the handles. Tightening knob 25 222 to engage protrusions 234, 236 may draw movable member 230 toward the knob. FIG. 27 depicts engaged protrusions 234, 236. With pivot axis 238 of handles 210, 212 fixed, handle 210 may rotate relative to handle 212 when the handles are compressed towards each other.

With pivot axis 238 of handles 210, 212 fixed, a closure member driver coupled to adjuster by the driver engager may rotate towards an extender engager of the adjuster when the handles are moved towards each other. The closure member driver may rotate away from the extender engager when handles 210, 212 are separated from each other. Pivot axis 238 may be offset from a shaft of the driver and from the extender engager. Having pivot axis 238 offset (i.e., not between the shaft of the driver and the extender engager) may allow the adjuster to accommodate various curvatures of elongated member that can be positioned in collars of bone fastener assemblies coupled to vertebrae. The ability to accommodate the curvature of the elongated member may allow the adjuster to move a first bone fastener assembly towards a second bone fastener assembly. The ability to accommodate the curvature of the elongated member may allow a user to secure a closure member coupled to the first bone fastener assembly to the elongated member and first bone fastener assembly such that the collar of the first bone fastener assembly adjusts to the proper position when the closure member is tightened. In adjuster embodiments that are to be used only with elongated members of a predetermined curvature, the pivot axis of the handles may be located between the shaft of the driver and the extender engager. The pivot axis may be positioned to accommodate the known curvature of the elongated member.

Figure 28:
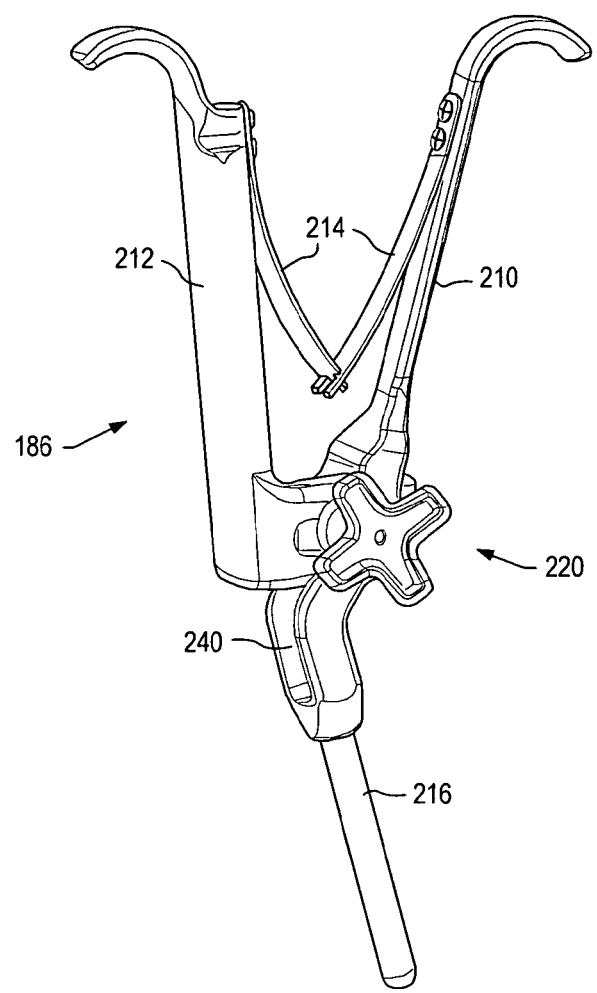
FIG. 28 depicts a perspective view of an embodiment of an adjuster.

FIG. 28 depicts an embodiment of adjuster 186 that may be used as a distractor. Adjuster 186 may include a bias system. In some embodiments, the bias system includes tension members 214 coupled to handles 210, 212. Handle 210 may align with handle 212 so that forces applied to the handles are directly opposed, thus eliminating or substantially eliminating torsional forces during use. Handle 210 may be coupled to an extender engager. In some embodiments, the extender engager may be shaft 216. In some embodiments, the extender engager may be a hollow shaft that fits over an extender. Shaft 216 may be positioned in a first extender that is coupled to a first collar secured to an elongated member of a spinal stabilization system. Handle 210 may include recess 240 above the extender engager. Recess 240 may accommodate a portion of a driver shaft to allow adjuster 186 to be coupled to extenders that are close together.

In some embodiments, adjuster 186 may include an adjustable pivot axis. The pivot axis may be adjusted using engagement mechanism 220. FIG. 25 depicts a partial cut-away view of engagement mechanism 220 with handle 212. FIG. 26 depicts engagement mechanism in a position that permits translation of handle 210 relative to handle 212. FIG. 27 depicts engagement mechanism in a position that inhibits translation of handle 210 relative to handle 212. When engagement mechanism is in the position that inhibits translation of handle 210 relative to handle 212, handle 210 is able to rotate relative to handle 212 about pivot axis 238 to allow for distraction of vertebrae.

Bone fastener assemblies that are coupled to extenders may be positioned in pedicles of vertebrae that are to be stabilized. An elongated member may be cut to length and contoured as desired. A medical practitioner may use experience and judgment to determine curvature of the elongated member for a patient. Determination of a desired curvature for the elongated member may be facilitated using radiological images of the patient. In some embodiments, a curvature of the elongated member may be chosen such that, when the elongated member is secured to the collars of the bone fastener assemblies, extenders coupled to the bone fastener assemblies cross at a surface of the skin. Crossing of the extenders at a surface of the skin allows the medical practitioner to minimize incision length and trauma to the patient. The elongated member may be bent or shaped with a tool (e.g., a rod bender) to allow insertion of the elongated member through channels of extenders with various spatial locations and/or various angular orientations.

Figure 29:
FIG. 29 depicts an embodiment of an elongated member.
Figure 30:
FIG. 30 depicts an embodiment of an elongated member.
Figure 31:
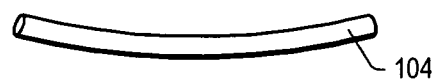
FIG. 31 depicts an embodiment of an elongated member.
Figure 32:
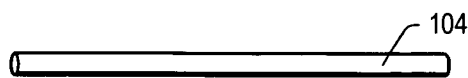
FIG. 32 depicts an embodiment of an elongated member.

An elongated member may be used to provide a desired shape to the spine of a patient. Elongated members may have shapes including, but not limited to, straight, bent, curved, s-shaped, and z-shaped. FIG. 29 depicts an embodiment of S-shaped elongated member 104. FIG. 30 depicts an embodiment of angled elongated member 104. FIG. 31 depicts an embodiment of bent elongated member 104. FIG. 32 depicts an embodiment of straight elongated member 104.

In some embodiments, elongated members 104 may have a substantially circular longitudinal cross section. In certain embodiments, elongated members 104 may have other cross-sectional shapes including, but not limited to, regular shapes (oval, rectangular, rhomboidal, square) and irregular shapes. An instrumentation kit for a spinal stabilization system may include straight rods and/or pre-shaped rods. Straight rods and/or pre-shaped rods may be contoured to accommodate patient anatomy if needed during the surgical procedure.

Prior to insertion of the elongated member, a tissue wedge or targeting needle may be used to wand between the bone fasteners to ensure a clean tissue plane has been formed between the bone fasteners. An end of the elongated member may be inserted at an angle or substantially longitudinally in a passage and/or channel of an extender coupled to a bone fastener assembly. Inserting the elongated member down two or more extenders and through an open path (i.e., the tissue plane) may allow a medical practitioner to avoid surgical difficulties associated with anatomical abnormalities and/or misalignment of system components. A positioning tool may be used to guide the elongated member down the extenders into slots in the collars.

During some surgical procedures, a first bone fastener assembly positioned in a vertebra may be moved along an elongated member towards a second bone fastener positioned in a second vertebra to achieve compression. An adjuster may be used to compress one or more vertebral levels of a patient's spine. Compression may be performed sequentially at different levels of a multi-level stabilization system. An adjuster may be used by itself or in combination with one or more other instruments during a spinal stabilization procedure to achieve compression of vertebrae.

Figure 33:
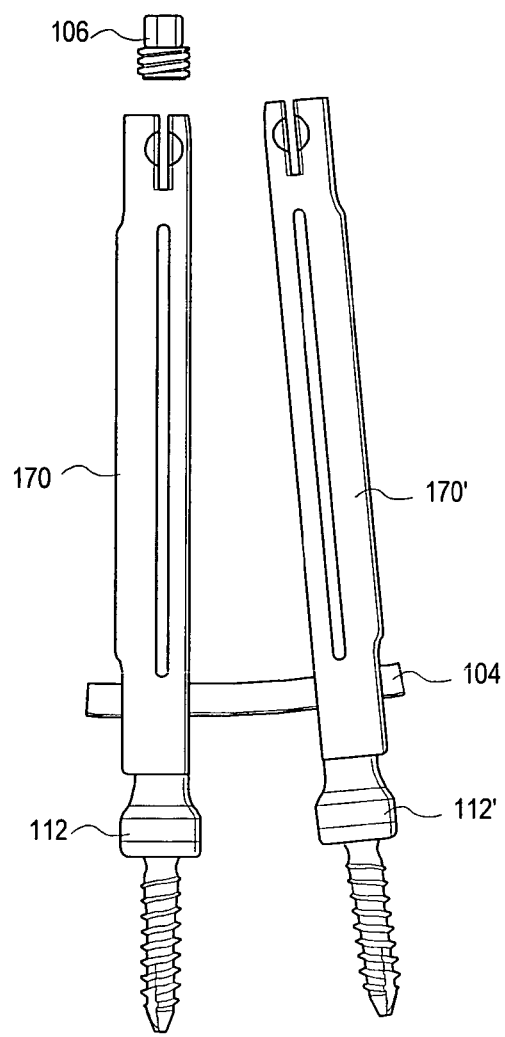
FIG. 33 depicts an embodiment of a spinal stabilization system before compression.

Adjuster 186 depicted in FIG. 24 may be used to compress vertebral bodies coupled to a spinal stabilization system. Adjuster 186 may be used with extenders of various shapes and/or sizes (e.g., lengths) to compress one or more vertebral levels. Before compression is initiated, elongated member 104 may be positioned in collars 112, 112' coupled to extenders 170, 170', as depicted in FIG. 33. Elongated member 104 may be seated in collars 112, 112'. Closure member 106 may be positioned in collar 112. Closure member 106 may be secured (e.g., tightened without shearing off the tool portion) in collar 112 to fix elongated member 104 in collar 112. In some embodiments, the tool portion of the closure member may be sheared off. Tightening closure member 106 may align extender 170 substantially perpendicular to elongated member 104. A second closure member may be coupled to a closure member driver.

The closure member driver may be coupled to the driver engager of the adjuster. A shaft of the closure member driver may be significantly longer than the length of the adjuster.

Knob 222 of adjuster 186 may be rotated so that engagement mechanism 220 allows translation of handle 210 relative to handle 212. Engagement mechanism 220 may be in an unengaged position as represented in FIG. 26.

Figure 34:
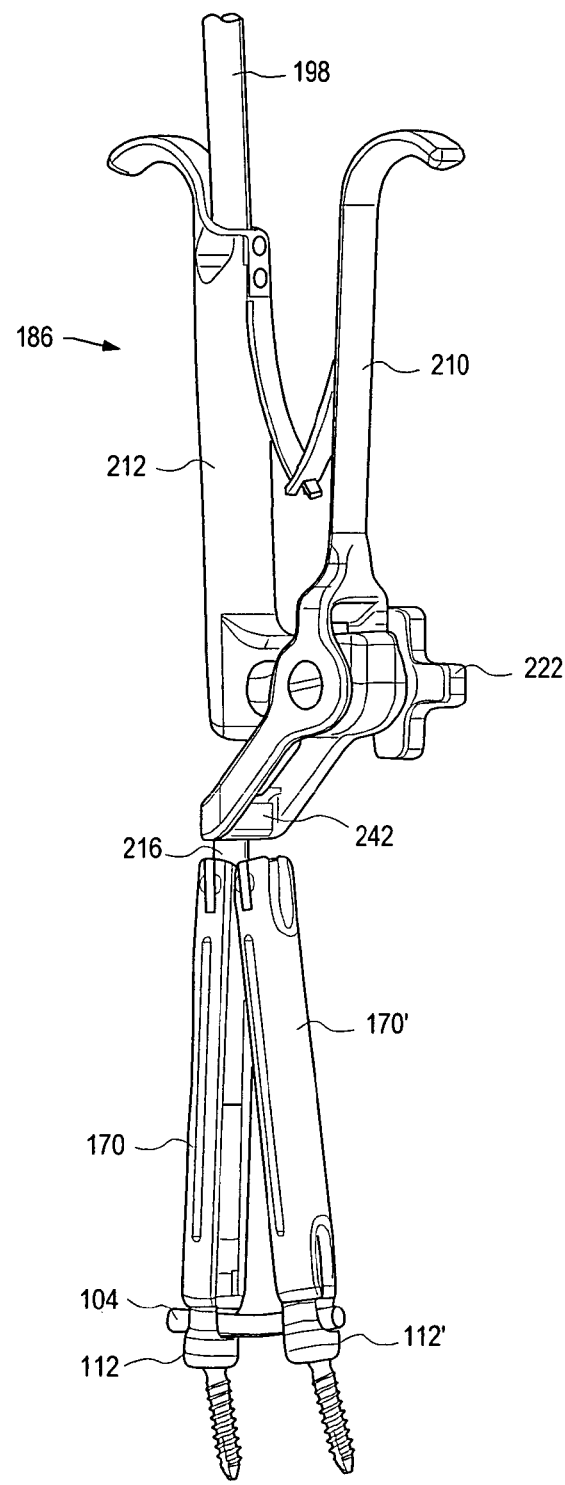
FIG. 34 depicts an embodiment of an adjuster with a shaft of the adjuster inserted in an extender coupled to a spinal stabilization system.
Figure 35:
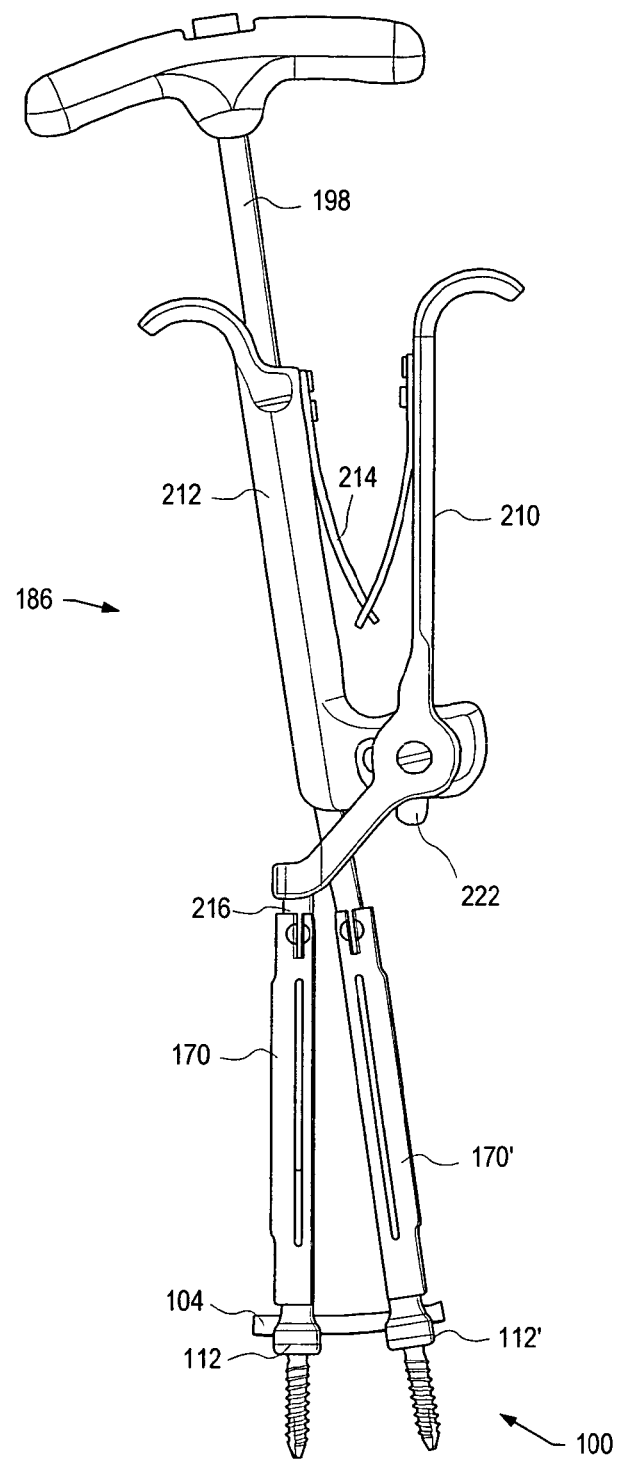
FIG. 35 depicts an embodiment of an adjuster with a shaft of the adjuster and a driver inserted in extenders coupled to a spinal stabilization system before compression.

As depicted in FIG. 34, shaft 216 of adjuster 186 may be positioned in extender 170 coupled to collar 112. Having the engagement mechanism in an unengaged position allows adjuster 186 to accommodate the separation distance between extenders 170, 170'. Extender 170' may be moved and/or handles 210, 212 may be squeezed to facilitate insertion of driver 198 in extender 170'. FIG. 35 depicts adjuster 186 with shaft 216 positioned in extender 170 and driver 198 positioned in extender 170'. In some embodiments, the driver may be positioned in extender 170' prior to the insertion of shaft 216 in extender 170.

Driver 198 may be rotated in a first direction to seat threading of the closure member in threading of the collar coupled to extender 170'. Driver 198 may be rotated in the first direction until the closure member contacts elongated member 104. Driver 198 may then be rotated in the opposite direction 0.5 to 4 turns to loosen the closure member. Loosening the closure member provides space between the closure member, the collar and elongated member 104 that allows the collar to be moved relative to the elongated member during compression.

When shaft 216 is positioned in extender 170, driver 198 is positioned in extender 170', and knob 222 is loosened to allow for translation of handle 210 relative to handle 212, tension members 214 may force handle 210 away from handle 212 so that the driver is positioned against an end surface of handle 210 (end surface 242 depicted in FIG. 34). Some separation distance is needed between driver 198 and the end surface to allow handle 210 to rotate relative to handle 212 when knob 222 has been tightened. To establish a separation distance between driver 198 and the end surface, handles 210, 212 may be squeezed so that handle 210 translates towards handle 212. When a desired separation between the end surface and the shaft of the driver is established, knob 222 may be tightened so that translation of handle 210 relative to handle 212 is inhibited. FIG. 27 depicts engagement mechanism 220 when knob 222 is tightened.

Referring to FIG. 35, when knob 222 is tightened to inhibit translation of handle 210 relative to handle 212, handle 212 is able to rotate relative to handle 210. With shaft 216 positioned in extender 170 and driver 198 positioned through adjuster 186 and in extender 170', handles 210, 212 may be squeezed so that handle 212 rotates relative to handle 210. Rotation of handle 212 relative to handle 210 may force extender 170' towards extender 170. When extender 170' is forced towards extender 170, collar 112' of a bone fastener assembly that is coupled to a first vertebra may be moved towards collar 112 of a bone fastener assembly that is coupled to a second vertebra, resulting in compression of the vertebrae. During activation of handles 210, 212 to cause compression, shaft 216 is able to move longitudinally in extender 170 and handle 212 is able to move longitudinally relative to driver to accommodate height change due to change in position of collar 112' relative to elongated member 104 and/or due to height change due to rotation of handle 212 relative to handle 210.

Figure 36:
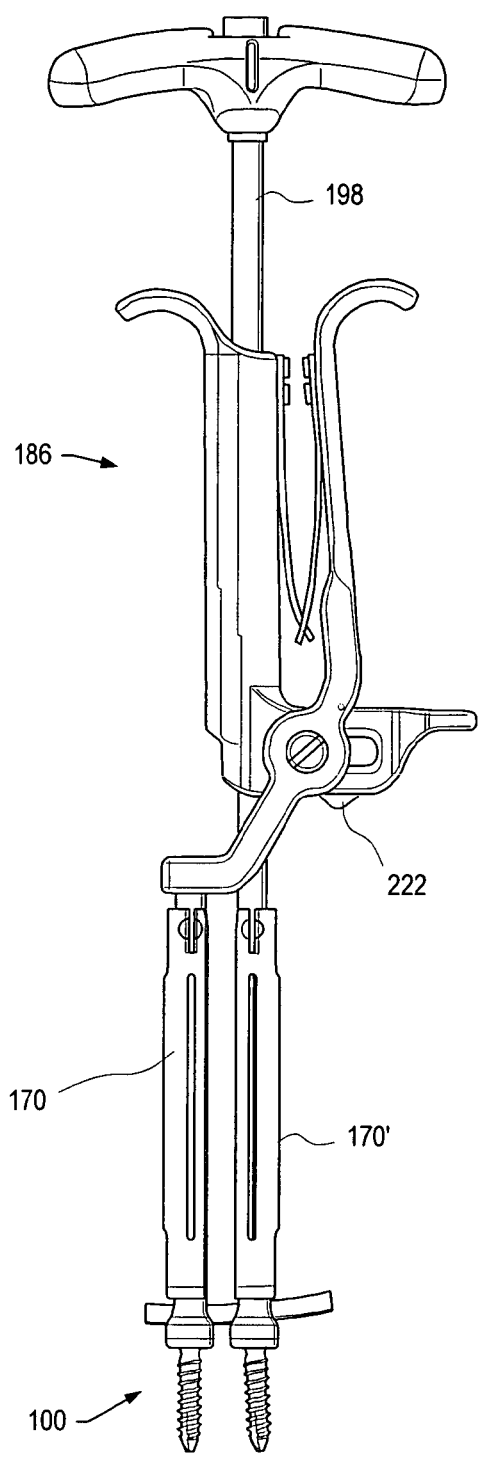
FIG. 36 depicts an embodiment of an adjuster following compression of a single-level spinal stabilization system.

When a desired amount of compression is achieved, driver 198 may be used to secure the closure member to collar 112' to fix a position of the collar relative to elongated member 104. Tightening the closure member against elongated member 104 may cause collar 112' and extender 170' to rotate so that the collar is oriented substantially perpendicular to the elongated member and the elongated member is fully seated in the collar. FIG. 36 depicts spinal stabilization system 100 after compression with adjuster 186.

The closure member in extender 170' may be released from driver 198. Driver 198 and adjuster 186 may be removed from extenders 170, 170'. A counter torque wrench and the driver may be used to shear off the tool portions of the closure members if the stabilization system is in the desired position.

Figure 37:
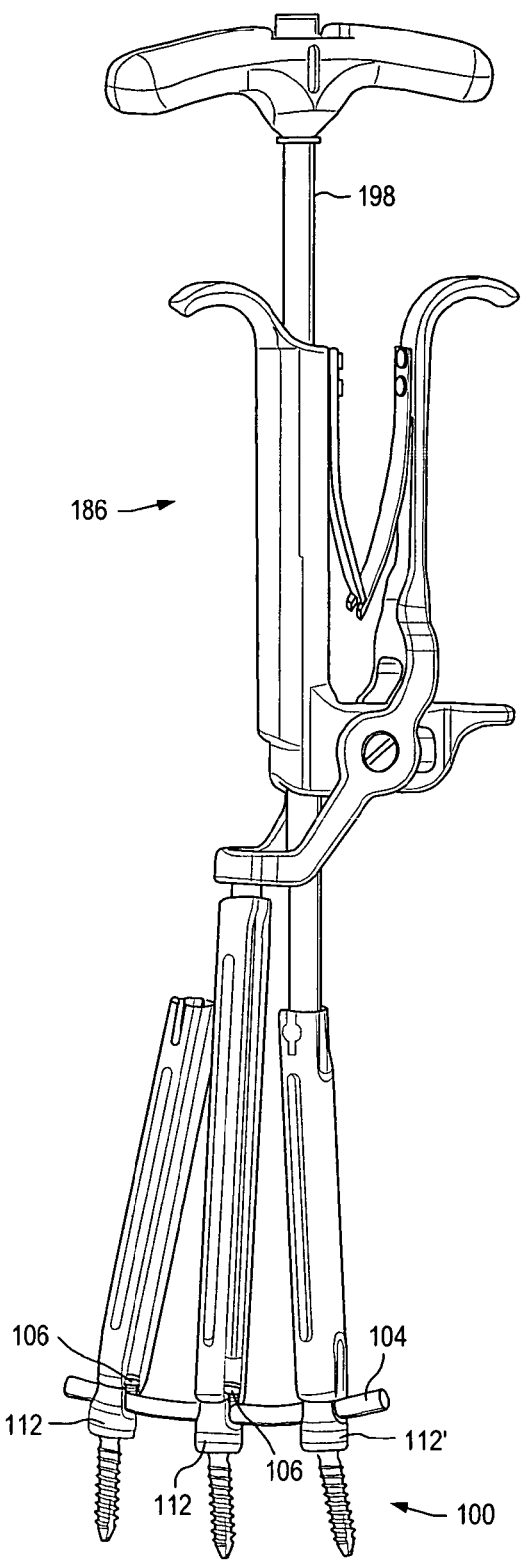
FIG. 37 depicts an embodiment of an adjuster during a stage of compression of a multilevel spinal stabilization system.

FIG. 37 depicts compression of multi-level spinal stabilization system 100 with adjuster 186. Closure members 106 positioned in collars 112 and tightened against elongated member 104 may inhibit movement of the collars relative to the elongated member. A closure member positioned in collar 112' may initially be loose to allow movement of the collar relative to elongated member 104, but the closure member may be tightened using driver 198 when adjuster 186 has positioned the collar at a desired location. In an embodiment, collars 112 may be components of bone fastener assemblies that are positioned in the L4 and L5 vertebrae. Collar 112' may be positioned in S1.

During some surgical procedures, a first bone fastener assembly positioned in a vertebra may be moved along an elongated member away from a second bone fastener positioned in a second vertebra to achieve distraction. An adjuster may be used to distract one or more vertebral levels of a patient's spine. Distraction may be performed sequentially at different levels of a multi-level stabilization system. An adjuster may be used by itself or in combination with one or more other instruments during a spinal stabilization procedure to achieve distraction of vertebrae.

Adjuster 186 depicted in FIG. 28 may be used to distract vertebral bodies coupled to a spinal stabilization system. Adjuster 186 may be used with extenders of various shapes and/or sizes (e.g., lengths) to distract one or more vertebral levels. Before distraction is initiated, elongated member 104 may be positioned in collars 112, 112' coupled to extenders 170, 170', as depicted in FIG. 33. Elongated member 104 may be seated in collars 112, 112'. Closure member 106 may be positioned in collar 112. Closure member 106 may be secured (e.g., tightened without shearing off the tool portion) in collar 112 to fix elongated member 104 in collar 112. Tightening closure member 106 may align extender 170 substantially perpendicular to elongated member 104. A second closure member may be coupled to a closure member driver. The closure member driver may be coupled to the driver engager of the adjuster.

Knob 222 of adjuster 186 may be rotated so that engagement mechanism 220 allows translation of handle 210 relative to handle 212. Engagement mechanism 220 may be in an unengaged position as represented in FIG. 26.

Figure 38:
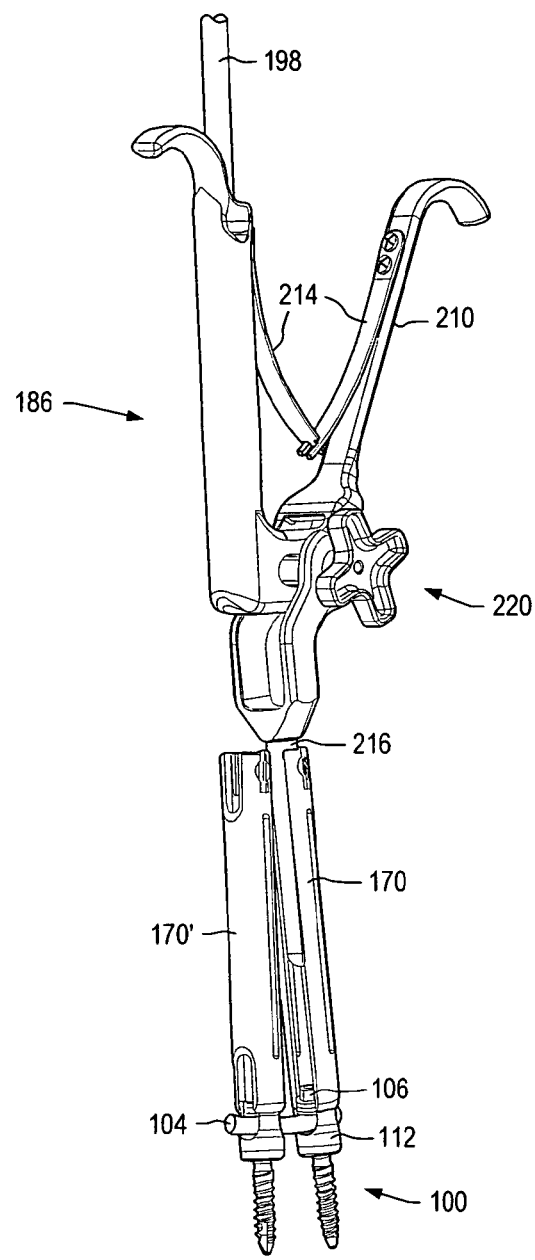
FIG. 38 depicts an embodiment of an adjuster with a shaft of the adjuster inserted in an extender coupled to a spinal stabilization system.
Figure 39:
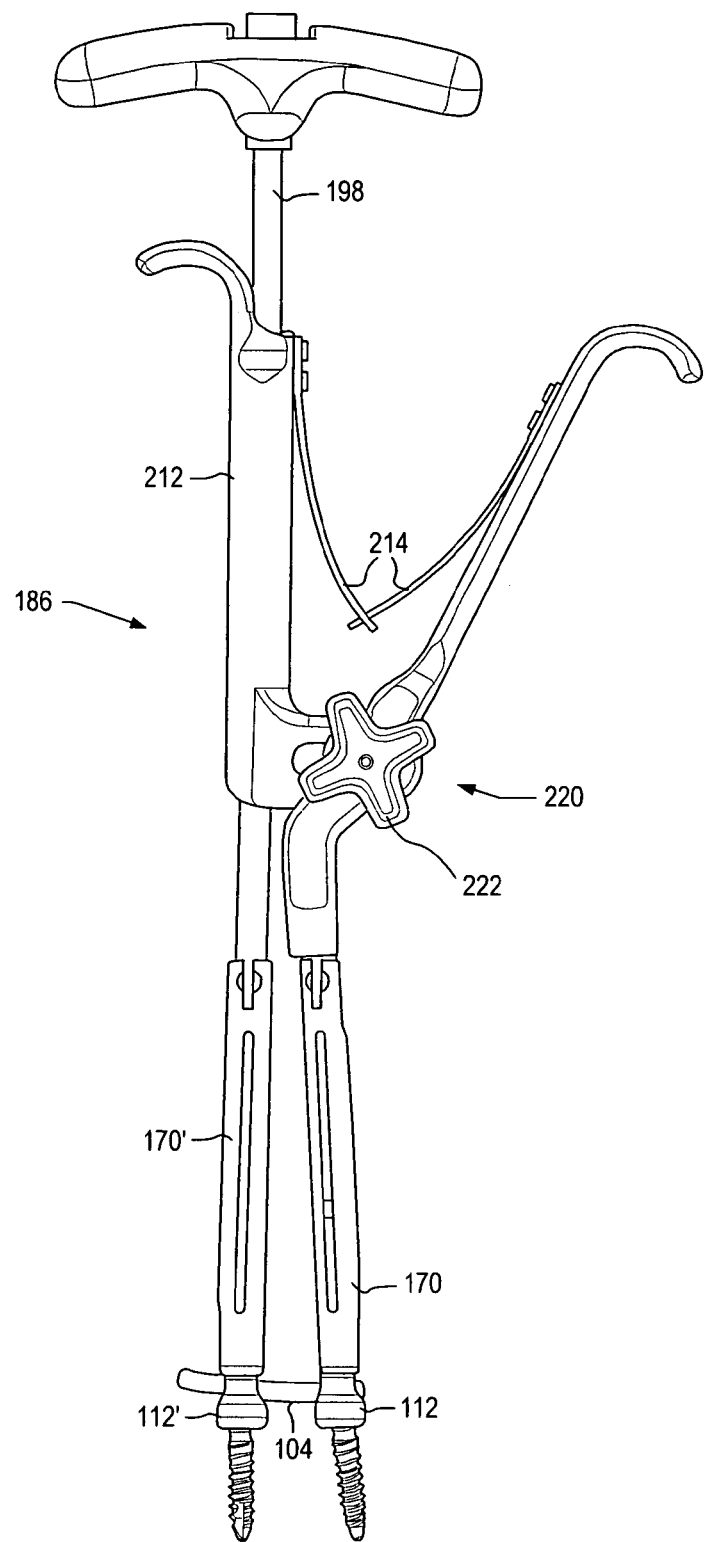
FIG. 39 depicts an embodiment of an adjuster with a shaft of the adjuster and a driver inserted in extenders coupled to a spinal stabilization system before distraction.

As depicted in FIG. 38, shaft 216 of adjuster 186 may be positioned in extender 170 coupled to collar 112. Elongated member 104 is secured to collar 112 by closure member 106. Having the engagement mechanism in an unengaged position allows adjuster 186 to accommodate the separation distance between extenders 170, 170'. Extender 170' may be moved and/or handles 210, 212 may be squeezed to facilitate insertion of driver 198 in extender 170'. FIG. 39 depicts adjuster 186 with shaft 216 positioned in extender 170 and driver 198 positioned through the adjuster in extender 170'. In some embodiments, the driver may be positioned through adjuster 186 into extender 170' prior to the insertion of shaft 216 in extender 170.

Driver 198 may be rotated in a first direction to seat threading of the closure member in threading of the collar coupled to extender 170'. Driver 198 may be rotated in the first direction until the closure member contacts elongated member 104. Driver 198 may then be rotated in the opposite direction 0.5 to 4 turns to loosen the closure member. Loosening the closure member provides space between the closure member, the collar and elongated member 104 that allows the collar to be moved relative to the elongated member during distraction.

When shaft 216 is positioned in extender 170 and driver 198 is positioned in extender 170', knob 222 may be tightened. Tightening knob 222 may inhibit translation of handle 210 towards or away from handle 212. When knob 222 is tightened to inhibit translation of handle 210 relative to handle 212, handle 212 is able to rotate relative to handle 210. With shaft 216 positioned in extender 170 and driver 198 positioned through adjuster 186 and in extender 170', handles 210, 212 may be squeezed so that handle 212 rotates relative to handle 210. Rotation of handle 212 relative to handle 210 may force extender 170' away from extender 170. When extender 170' is forced away from extender 170, collar 112' of a bone fastener assembly that is coupled to a first vertebra may be moved away from collar 112 of a bone fastener assembly that is coupled to a second vertebra, resulting in distraction of the vertebrae. During activation of handles 210, 212 to cause distraction, shaft 216 is able to move longitudinally in extender 170 and handle 212 is able to move longitudinally relative to driver to accommodate height change due to change in position of collar 112' relative to elongated member 104 and/or due to height change due to rotation of handle 210 relative to handle 212.

Figure 40:
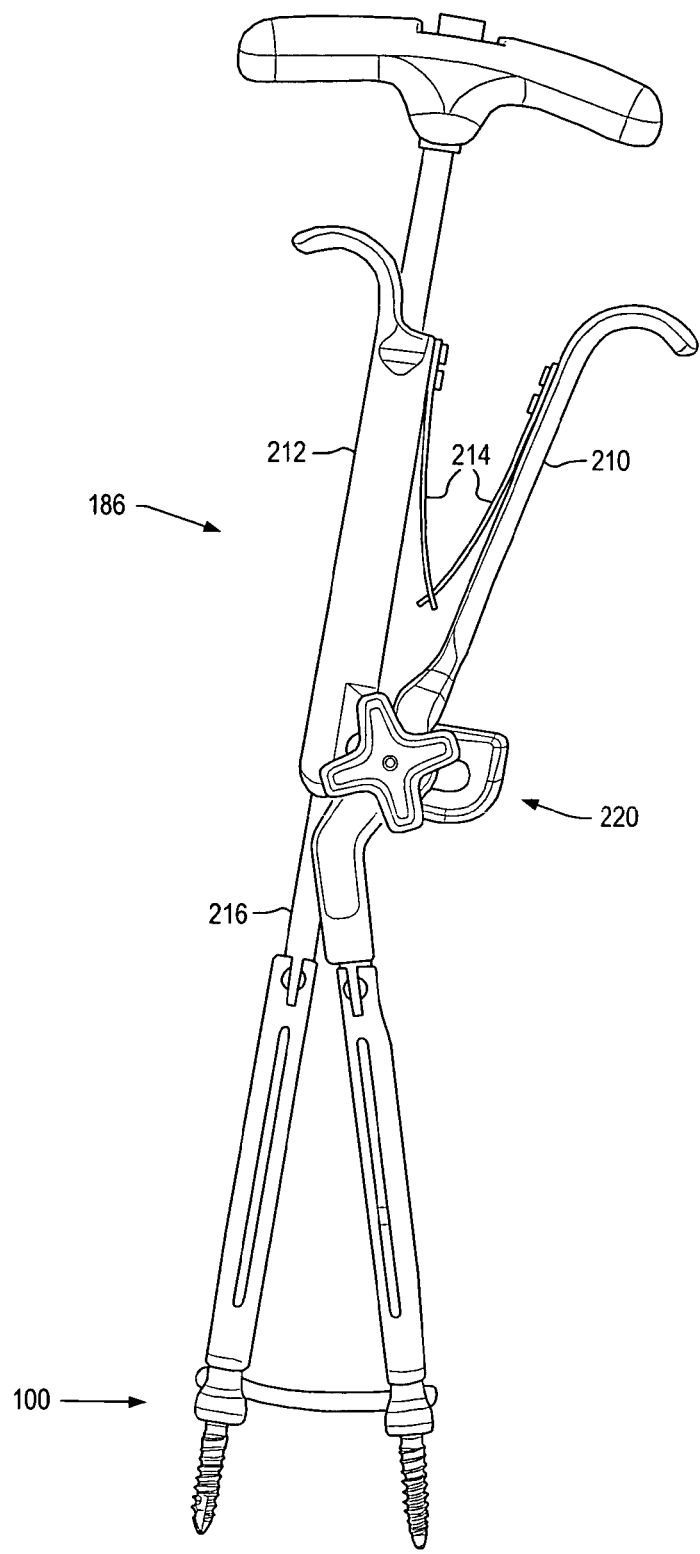
FIG. 40 depicts an embodiment of an adjuster following distraction.

When a desired amount of distraction is achieved, driver 198 may be used to secure the closure member to collar 112' to fix a position of the collar relative to elongated member 104. Tightening the closure member against elongated member 104 may cause collar 112' and extender 170' to rotate so that the collar is oriented substantially perpendicular to the elongated member and the elongated member is fully seated in the collar. FIG. 40 depicts spinal stabilization system 100 after distraction with adjuster 186.

The closure member in extender 170' may be released from driver 198. Driver 198 and adjuster 186 may be removed from extenders 170, 170'. A counter torque wrench and the driver may be used to shear off the tool portions of the closure members if the stabilization system is in the desired position.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed:

1. A system for adjusting a distance between vertebral bodies of a human spine, comprising:
   a first extender configured to detachably couple to a first bone fastener assembly that is securable to a first vertebral body;
   a second extender configured to detachably couple to a second bone fastener assembly that is securable to a second vertebral body, wherein one of the first and second bone fastener assemblies secures to a rod so as to inhibit movement relative to the rod, and the other of the first and second bone fastener assemblies is movably coupled to the rod to allow movement along the rod relative to the secured bone fastener assembly; and
   an adjuster having:
      a handle having a longitudinal axis;
      a pivot member coupled to a first end of the handle, the pivot member including a driver engager; and
      a shaft coupled to the first end of the handle, the shaft extending substantially perpendicular to the handle, the shaft configured to engage one of the first and second extenders.

2. The system of claim 1, wherein the pivot member includes a pivot element that rotates freely within a holder, wherein the holder is attached to the handle.

3. The system of claim 1, wherein the shaft is attached to the handle at a fixed angle.

4. The system of claim 1, wherein the pivot member is offset laterally from the shaft.

5. The system of claim 1, wherein the pivot member is aligned along the longitudinal axis with the shaft.

6. The system of claim 1, wherein the shaft is configured to be received within one of the first and second extenders.

7. The system of claim 1, wherein actuation of a driver engaged with the driver engager towards the handle at the pivot member forces the extender that is coupled to the bone fastener assembly movably coupled to the rod to move away from the extender that is coupled to the bone fastener assembly secured to the rod, whereby the bone fastener assembly movably coupled to the rod is forced to move away from the bone fastener assembly secured to the rod, causing distraction of the first and second vertebral bodies.

8. The system of claim 1, wherein actuation of a driver engaged with the driver engager away from the handle at the pivot member forces the extender that is coupled to the bone fastener assembly movably coupled to the rod to move towards the extender that is coupled to the bone fastener assembly secured to the rod, whereby the bone fastener assembly movably coupled to the rod is forced to move towards the bone fastener assembly secured to the rod, causing compression of the first and second vertebral bodies.

9. The system of claim 1, wherein the driver engager includes an opening configured to receive the driver.

10. A system for adjusting a distance between vertebral bodies of a human spine, comprising:
    a first extender configured to detachably couple to a first bone fastener assembly that is securable to a first vertebral body;
    a second extender configured to detachably couple to a second bone fastener assembly that is securable to a second vertebral body, wherein one of the first and second bone fastener assemblies secures to a rod so as to inhibit movement relative to the rod, and the other of the first and second bone fastener assemblies is movably coupled to the rod to allow movement along the rod relative to the secured bone fastener assembly; and an adjuster having:
: a handle having a longitudinal axis;
: a pivot member coupled to a first end of the handle, the pivot member including a driver engager; and
: a shaft coupled to the first end of the handle, the shaft extending substantially perpendicular to the handle, the shaft configured to engage one of the first and second extenders;
: wherein actuation of a driver engaged with the driver engager relative to the handle at the pivot member forces the extender that is coupled to the bone fastener assembly movably coupled to the rod to move relative to the extender that is coupled to the bone fastener assembly secured to the rod, whereby the bone fastener assembly movably coupled to the rod is forced to move relative to the bone fastener assembly secured to the rod, causing compression or distraction of the first and second vertebral bodies.

11. The system of claim 10, wherein the driver engager includes an opening configured to receive the driver.

12. The system of claim 10, wherein the pivot member includes a pivot element that rotates freely within a holder, wherein the holder is attached to the handle.

13. The system of claim 10, wherein the shaft is attached to the handle at a fixed angle.

14. The system of claim 10, wherein the pivot member is offset laterally from the shaft.

15. The system of claim 10, wherein the pivot member is aligned along the longitudinal axis with the shaft.

16. The system of claim 10, wherein the shaft is configured to be received within one of the first and second extenders.

17. A method of adjusting a distance between vertebral bodies of a human spine, comprising:
: securing first and second bone fastener assemblies to first and second vertebra, respectively;
: coupling first and second extenders to the first and second bone fastener assemblies, respectively;
: securing the first bone fastener assembly to a rod to inhibit movement of the first bone fastener assembly relative to the rod;
: coupling the rod to the second bone fastener assembly, wherein the second bone fastener assembly is movable along the rod;
: coupling an adjuster to the first extender via a shaft of the adjuster, wherein the shaft is attached to a handle of the adjuster;
: inserting a driver through a pivot member of the adjuster into the second extender, wherein the handle is coupled to the pivot member and the driver is inserted through a pivot point;
: actuating the driver relative to the handle at the pivot point to move the second extender relative to the first extender, thereby causing the second bone fastener assembly secured to the second vertebra to move relative to the first bone fastener assembly secured to the first vertebra, thereby adjusting a distance between the first vertebra and the second vertebra.

18. The method of claim 17, wherein the shaft is attached to the handle at a fixed angle.

19. The method of claim 17, wherein inserting the driver through the pivot member includes inserting the driver through an opening in the pivot member wherein the opening is offset laterally from the shaft.

20. The method of claim 17, wherein inserting the driver through the pivot member includes inserting the driver through an opening in the pivot member wherein the opening is aligned along a longitudinal axis of the handle.

* * * * *